United States Patent
Cameron et al.

[11] Patent Number: 6,124,314
[45] Date of Patent: Sep. 26, 2000

[54] OSTEOPOROSIS COMPOUNDS

[75] Inventors: Kimberly O. Cameron, East Lyme; Bruce A. Lefker, Gales Ferry; Robert L. Rosati, Stonington, all of Conn.

[73] Assignee: Pfizer Inc., New York, N.Y.

[21] Appl. No.: 09/161,797

[22] Filed: Sep. 28, 1998

Related U.S. Application Data

[60] Provisional application No. 60/061,592, Oct. 10, 1997.

[51] Int. Cl.⁷ .................. A61K 31/47; A61K 31/445; A61K 31/40
[52] U.S. Cl. .................. 514/307; 514/317; 514/424; 514/529; 514/578; 514/613
[58] Field of Search .............. 562/536; 514/578, 514/529, 613, 307, 317, 424

[56] References Cited

U.S. PATENT DOCUMENTS

| | | | |
|---|---|---|---|
| 3,987,091 | 10/1976 | Cragoe, Jr. et al. | 260/490 |
| 3,991,087 | 11/1976 | Cragoe, Jr. et al. | 260/408 |
| 4,033,996 | 7/1977 | Cragoe, Jr. et al. | 260/490 |
| 4,066,692 | 1/1978 | Cragoe, Jr. et al. | 424/312 |
| 4,091,107 | 5/1978 | Cragoe, Jr. et al. | 424/274 |
| 4,092,356 | 5/1978 | Cragoe, Jr. et al. | 260/535 R |
| 4,097,504 | 6/1978 | Cragoe, Jr. et al. | 260/405 |
| 4,112,236 | 9/1978 | Bicking et al. | 560/12 |

*Primary Examiner*—Zinna Northington Davis
*Attorney, Agent, or Firm*—Peter C. Richardson; Gregg C. Benson; Robert T. Ronau

[57] ABSTRACT

This invention relates to prostaglandin agonists, methods of using such prostaglandin agonists, pharmaceutical compositions containing such prostaglandin agonists and kits containing such prostaglandin agonists. The prostaglandin agonists are useful for the treatment of bone disorders including osteoporosis.

17 Claims, No Drawings

OSTEOPOROSIS COMPOUNDS

CROSS-REFERENCE TO RELATED APPLICATIONS

This application is a non-provisional application based on U.S. provisional application No. 60/061,592 Oct. 10, 1997.

BACKGROUND OF INVENTION

This invention relates to prostaglandin agonists, pharmaceutical compositions containing such agonists and the use of such agonists to prevent bone loss or restore or augment bone mass and to enhance bone healing including the treatment of conditions which present with low bone mass and/or bone defects in vertebrates, and particularly mammals, including humans.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

There are currently two main types of pharmaceutical therapy for the treatment of osteoporosis. The first is the use of anti-resorptive compounds to reduce the resorption of bone tissue.

Estrogen is an example of an anti-resorptive agent. It is known that estrogen reduces fractures. In addition, Black, et al. in EP 0605193A1 report that estrogen, particularly when taken orally, lowers plasma levels of LDL and raises those of the beneficial high density lipoproteins (HDL's). However, estrogen failed to restore bone back to young adult levels in the established osteoporotic skeleton. Furthermore, long-term estrogen therapy, however, has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis that have the desirable effect on serum LDL but do not cause undesirable effects.

A second type of pharmaceutical therapy for the treatment of osteoporosis is the use of anabolic agents to promote bone formation and increase bone mass. This class of agents is expected to restore bone to the established osteoporotic skeleton.

U.S. Pat. No. 4,112,236, incorporated herein by reference, discloses certain interphenylene 8-aza-9-dioxothia-11,12-secoprostaglandins for the treatment of patients with renal impairment.

Certain prostagladin agonists are disclosed in GB 1478281, GB1479156 and U.S. Pat. Nos. 4,175,203, 4,055,596, 4,175,203, 3,987,091 and 3,991,106 as being useful as, for example, renal vasodilators. U.S. Pat. Nos. 4,175,203, 4,055,596, 4,175,203, 3,987,091 and 3,991,106 are each incorporated herein by reference.

U.S. Pat. No. 4,033,996, which is incorporated herein by reference, discloses certain 8-aza-9-oxo(and dioxo)-thia-11,12-secoprostaglandins which are useful as renal vasodilators, for the prevention of thrombus formation, to induce growth hormone release, and as regulators of the immune response.

French Pat. No. 897,566 discloses certain amino acid derivatives for the treatment of neurological, mental or cardiovascular disease.

J. Org. Chem. 26; 1961; 1437 discloses N-acetyl-N-benzyl-p-aminophenylmercaptoacetic acid.

Certain 11,12-secoprostaglandins are disclosed in U.S. Pat. Nos. 3,991,087 and 4,066,692, each of which is incorporated herein by reference.

In addition to osteoporosis, approximately, 20–25 million women and an increasing number of men have detectable vertebral fractures as a consequence of reduced bone mass, with an additional 250,000 hip fractures reported yearly in America alone. The latter case is associated with a 12% mortality rate within the first two years and with a 30% rate of patients requiring nursing home care after the fracture. While this is already significant, the economic and medical consequences of convalescence due to slow or imperfect healing of these bone fractures is expected to increase, due to the aging of the general population.

Estrogens have been shown (Bolander et al., 38th Annual Meeting Orthopedic Research Society, 1992) to improve the quality of the healing of appendicular fractures. Therefore, estrogen replacement therapy might appear to be a method for the treatment of fracture repair. However, patient compliance with estrogen therapy is relatively poor due to its side effects, including the resumption of menses, mastodynia, an increased risk of uterine cancer, an increased perceived risk of breast cancer, and the concomitant use of progestins. In addition, men are likely to object to the use of estrogen treatment. Clearly the need exists for a therapy which would be beneficial to patients who have suffered debilitating bone fractures and which would increase patient compliance.

Although there are a variety of osteoporosis therapies there is a continuing need and a continuing search in this field of art for alternative osteoporosis therapies. In addition, there is a need for bone fracture healing therapies. Also, there is a need for therapy which can promote bone re-growth into skeletal areas where defects exist such as defects caused or produced by, for example, tumors in bone. Further, there is a need for therapy which can promote bone re-growth into skeletal areas where bone grafts are indicated.

SUMMARY OF THE INVENTION

This invention is directed to a compound of Formula I

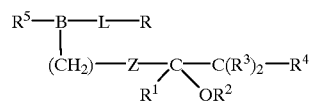

a prodrug thereof or a pharmaceutically acceptable salt of said compound or said prodrug, wherein:

B is N or C(Q$^1$), where Q$^1$ is H or (C$_1$–C$_3$)alkyl;

L is n-propylenyl-X— or CH$_2$-metaphenylene-CH$_2$, wherein X is furanyl, thienyl, thiazolyl or tetrahydrofuranyl, said $CH_2$-metaphenylene-$CH_2$ or X being optionally mono-, di- or tri-substituted on aromatic carbon independently with one to three chloro, fluoro, methoxy, difluoromethoxy, trifluoromethoxy, trifluoromethyl or methyl;

R is carboxyl, $(C_1-C_6)$alkoxycarbonyl, tetrazolyl, 5-oxo-1,2,4-thiadiazolyl; 5-oxo-1,2,4-oxadiazolyl, $(C_1-C_4)$alkylsulfonylcarbamoyl or phenylsulfonylcarbamoyl;

$R^1$ is H, methyl, ethyl or propyl;

$R^2$ is H or $(C_2-C_5)$ alkanoyl;

$R^3$ is independently H, fluoro or methyl;

$R^4$ is H, $(C_1-C_7)$ alkyl, or $R^4$ and $R^1$ are taken together to form a 5–9 membered carbocyclic ring, said alkyl being optionally monounsaturated and optionally mono-, di- or tri-substituted independently with one to three fluoro, chloro, methoxy, difluoromethoxy, trifluoromethoxy, trifluoromethyl or methyl;

$R^5$ is $(C_1-C_6)$alkylsulfonyl, $(C_3-C_7)$cycloalkylsulfonyl, $(C_3-C_7)$cycloalkyl$(C_1-C_6)$alkylsulfonyl, $(C_1-C_6)$alkylcarbonyl, $(C_3-C_7)$cycloalkylcarbonyl, $(C_3-C_7)$cycloalkyl$(C_1-C_6)$alkylcarbonyl, G-sulfonyl or G-carbonyl, said $(C_1-C_6)$alkylsulfonyl, $(C_3-C_7)$cycloalkylsulfonyl, $(C_3-C_7)$cycloalkyl$(C_1-C_6)$alkylsulfonyl, $(C_1-C_6)$alkylcarbonyl, $(C_3-C_7)$cycloalkylcarbonyl, $(C_3-C_7)$cycloalkyl$(C_1-C_6)$alkylcarbonyl optionally mono-, di- or tri-substituted on carbon independently with hydroxy, fluoro, chloro, methoxy, difluoromethoxy, trifluoromethoxy, trifluoromethyl or methyl;

Z is methylene, ethylene, propylene or ethenylene;

G is Ar, $Ar^1$-V-$Ar^2$, Ar-$(C_1-C_6)$alkylene, Ar-CONH-$(C_1-C_6)$alkylene, $R^{12}R^{13}$-amino, oxy$(C_1-C_6)$alkylene, amino substituted with Ar, or amino substituted with Ar$(C_1-C_4)$alkylene and $R^{11}$, wherein $R^{11}$ is H or $(C_1-C_8)$alkyl, $R^{12}$ and $R^{13}$ may be taken separately and are independently selected from H and $(C_1-C_8)$alkyl, or $R^{12}$ and $R^{13}$ are taken together with the nitrogen atom to which they are attached to form a five- or six-membered azacycloalkyl, said azacycloalkyl optionally containing an oxygen atom and optionally substituted with up to two oxo, hydroxy, $(C_1-C_4)$alkyl, fluoro or chloro;

Ar is a partially saturated or fully unsaturated five to eight membered ring optionally having one to four heteroatoms selected independently from oxygen, sulfur and nitrogen, or a bicyclic ring consisting of two fused independently partially saturated, fully saturated or fully unsaturated five or six membered rings, taken independently, optionally having one to four heteroatoms selected independently from nitrogen, sulfur and oxygen, or a tricyclic ring consisting of three fused independently partially saturated, fully saturated or fully unsaturated five or six membered rings, optionally having one to four heteroatoms selected independently from nitrogen, sulfur and oxygen, said partially or fully saturated ring, bicyclic ring or tricyclic ring optionally having one or two oxo groups substituted on carbon or one or two oxo groups substituted on sulfur; or Ar is a fully saturated five to seven membered ring having one or two heteroatoms selected independently from oxygen, sulfur and nitrogen;

$Ar^1$ and $Ar^2$ are each independently a partially saturated, fully saturated or fully unsaturated five to eight membered ring optionally having one to four heteroatoms selected independently from oxygen, sulfur and nitrogen, or a bicyclic ring consisting of two fused independently partially saturated, fully saturated or fully unsaturated five or six membered rings, taken independently, optionally having one to four heteroatoms selected independently from nitrogen, sulfur and oxygen, or a tricyclic ring consisting of three fused independently partially saturated, fully saturated or fully unsaturated five or six membered rings, taken independently, optionally having one to four heteroatoms selected independently from nitrogen, sulfur and oxygen, said partially or fully saturated ring, bicyclic ring or tricyclic ring optionally having one or two oxo groups substituted on carbon or one or two oxo groups substituted on sulfur;

said Ar, $Ar^1$ and $Ar^2$ moieties are optionally substituted on carbon or nitrogen, on one ring if the moiety is monocyclic, on one or both rings if the moiety is bicyclic, or on one, two or three rings if the moiety is tricyclic, with up to three substituents per moiety, independently selected from $R^{14}$, $R^{15}$ and $R^{16}$ wherein $R^{14}$, $R^{15}$ and $R^{16}$ are independently hydroxy, nitro, halo, carboxy, $(C_1-C_7)$alkoxy, $(C_1-C_4)$alkoxy$(C_1-C_4)$alkyl, $(C_1-C_4)$alkoxycarbonyl, $(C_1-C_7)$alkyl, $(C_2-C_7)$alkenyl, $(C_2-C_7)$alkynyl, $(C_3-C_7)$cycloalkyl, $(C_3-C_7)$cycloalkyl$(C_1-C_4)$alkyl, $(C_3-C_7)$cycloalkyl$(C_1-C_4)$alkanoyl, formyl, $(C_1-C_8)$alkanoyl, $(C_1-C_6)$alkanoyl$(C_1-C_6)$alkyl, $(C_1-C_4)$alkanoylamino, $(C_1-C_4)$alkoxycarbonylamino, hydroxysulfonyl, aminocarbonylamino or mono-N-, di-N,N-, di-N,N'- or tri-N,N,N'-$(C_1-C_4)$alkyl substituted aminocarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, $(C_1-C_6)$alkylthio, $(C_1-C_6)$alkylsulfinyl, $(C_1-C_4)$alkylsulfonyl or mono-N- or di-N,N-$(C_1-C_4)$alkylaminosulfinyl; and V is a bond, thio$(C_1-C_4)$alkylene, $(C_1-C_4)$alkylenethio, $(C_1-C_4)$alkyleneoxy, oxy$(C_1-C_4)$alkylene or $(C_1-C_3)$alkylene optionally mono- or di-substituted, when V is not a bond, independently with hydroxy or fluoro.

A preferred group of compounds of Formula I, designated Group A, comprises those compounds of claim 1, prodrugs thereof and pharmaceutically acceptable salts of said compounds and said prodrugs, wherein B is N; R is carboxyl, $(C_1-C_6)$alkoxycarbonyl or tetrazolyl; Z is ethylenyl; $R^1$ and $R^2$ are each H; and L is $CH_2$-metaphenylene-$CH_2$.

A preferred group of compounds within Group A comprises those compounds, prodrugs thereof and pharmaceutically acceptable salts of said compounds and said prodrugs, wherein $R^5$ is $(C_1-C_3)$alkylsulfonyl or $(C_3-C_7)$cycloalkylsulfonyl.

Another preferred group of compounds within Group A comprises those compounds, prodrugs thereof and pharmaceutically acceptable salts of said compounds and said prodrugs, wherein $R^5$ is G-sulfonyl and G is phenyl, imidazolyl, pyridyl, pyrazolyl or pyrimidyl optionally mono-, di- or tri-substituted on carbon or nitrogen with chloro, fluoro, methoxy, difluoromethoxy, trifluoromethoxy, trifluoromethyl or methyl.

Another preferred group of compounds within Group A comprises those compounds, prodrugs thereof and pharmaceutically acceptable salts of said compounds and said prodrugs, wherein $R^5$ is $(C_1-C_6)$alkylcarbonyl optionally mono-, di- or tri-substituted with hydroxy or fluoro.

Another preferred group of compounds of Formula I, designated Group B, comprises those compounds, prodrugs thereof and pharmaceutically acceptable salts of said compounds and said prodrugs, wherein B is N; R is carboxyl, (C$_1$–C$_6$)alkoxycarbonyl or tetrazolyl; Z is ethylenyl; R$^1$ and R$^2$ are each H; and L is n-propylenyl-X—.

A preferred group of compounds within Group B comprises those compounds, prodrugs thereof and pharmaceutically acceptable salts of said compounds and said prodrugs, wherein R$^5$ is (C$_1$–C$_6$)alkylsulfonyl or (C$_3$–C$_7$) cycloalkylsulfonyl.

Another preferred group of compounds within Group B comprises those compounds, prodrugs thereof and pharmaceutically acceptable salts of said compounds and said prodrugs, wherein R$^5$ is G-sulfonyl and G is phenyl, imidazolyl, pyridyl, pyrazolyl or pyrimidyl optionally mono-, di- or tri-substituted on carbon or nitrogen with chloro, fluoro, methoxy, difluoromethoxy, trifluoromethoxy, trifluoromethyl or methyl.

Another preferred group of compounds within Group B comprises those compounds; prodrugs thereof and pharmaceutically acceptable salts of said compounds and said prodrugs, wherein R$^5$ is (C$_1$–C$_6$)alkylcarbonyl optionally mono-, di- or tri-substituted with hydroxy or fluoro.

This invention is also directed to methods of using compounds of Formula II,

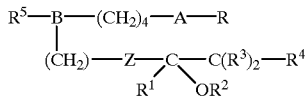

prodrugs thereof and pharmaceutically acceptable salts of said compounds and said prodrugs, wherein:

A is ethylene, n-propylene, α-methylethylene, β-methylethylene, α,α-dimethylethylene, β,β-dimethylethylene or oxymethylene;

B is N or C(Q);

R is carboxy, (C$_1$–C$_{10}$) alkoxycarbonyl, carbamoyl, mono-N- or di-N,N-(C$_1$–C$_4$)alkyl-substituted carbamoyl or —COOY wherein Y is 1-succinimidoethyl, 1-pivaloyloxyethyl, 2-acetamidoethyl, diloweralkylaminoloweralkyl, or carbazoyl;

R$^1$ is H, methyl, ethyl or propyl;

R$^2$ is H or (C$_2$–C$_5$) alkanoyl;

R$^3$ is independently H or methyl;

R$^4$ is H, (C$_1$–C$_4$) alkyl, vinyl or 2,2,2-trifluoroethyl; or R$^4$ and R$^1$ are taken together to form a 5–9 membered carbocyclic ring;

R$^5$, when B is C(Q), is formyl, acetyl, pivaloyl, propionyl, acryloyl, hydroxyacetyl, 3-hydroxypropionyl, hydroxymethyl, 1-hydroxyethyl, 1,2-dihydroxyethyl, 1,3-dihydroxypropyl or 1-hydroxyl-1-methylethyl;

R$^5$, when B is N, is formyl, acetyl, propionyl, acryloyl, hydroxyacetyl, 2,2,2-trifluoroethyl or R$^6$SOy;

Z is methylene, ethylene, n-propylene, tetramethylene, vinylene or ethynylene;

Q is H, chloro, bromo, methyl, phenyl or substituted phenyl;

R$^6$ is methyl, ethyl, propyl or isopropyl; and y is 1 or 2; , a prodrug thereof or a pharmaceutically acceptable salt of said compound or said prodrug as described below.

This invention is also directed to methods of using compounds of Formula III,

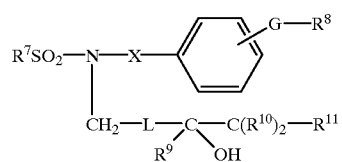

prodrugs thereof and pharmaceutically acceptable salts of said compounds and said prodrugs wherein:

R$^7$ is (C$_1$–C$_4$) alkyl;

R$^8$ is carboxy or (C$_1$–C$_{10}$) alkoxycarbonyl;

R$^9$ is H or methyl;

R$^{10}$ is independently H or methyl;

R$^{11}$ is (C$_3$–C$_6$) alkyl; or R$^{11}$ and R$^9$ are taken together to form a 5–9 membered carbocyclic ring;

G is (CH$_2$)$_n$, oxymethylene or vinylene;

X is (CH$_2$)$_m$;

L is ethylene, vinylene or ethynylene;

n is 0 or 2; and m is 1, 3 or 4; provided that the sum of chain-forming elements in G and X is limited to either 3 or 4, a prodrug thereof or a pharmaceutically acceptable salt of said compound or said prodrug as described below.

This invention is also directed to methods for treating vertebrates, e.g., a mammal, having a condition which presents with low bone mass comprising administering to said vertebrate, e.g., a mammal, having a condition which presents with low bone mass, a therapeutically effective amount of a compound of Formulas I, II or III above a prodrug thereof or a pharmaceutically acceptable salt of said compound or said prodrug. Preferably post-menopausal women and men over the age of 60 are treated. Also included are individuals regardless of age who have significantly reduced bone mass, i.e., greater than or equal to 1.5 standard deviations below young normal levels.

Yet another aspect of this invention is directed to methods for treating osteoporosis, bone fractures, osteotomy, bone loss associated with periodontitis, or prosthetic ingrowth in a vertebrate, e.g., a mammal (including a human being), comprising administering to said vertebrate, e.g., a mammal suffering from osteoporosis, bone fracture, osteotomy, bone loss associated with periodontitis, or prosthetic ingrowth an osteoporosis, bone fracture, osteotomy, bone loss associated with periodontitis, or prosthetic ingrowth treating amount of a compound of Formulas I, II or III, a prodrug thereof or a pharmaceutically acceptable salt of said compound or said prodrug.

Yet another aspect of this invention is directed to methods for treating osteoporosis in a vertebrate, e.g., a mammal (including a human being), comprising administering to said vertebrate, e.g., a mammal suffering from osteoporosis, an osteoporosis treating amount of a Formula I, II or III compound, a prodrug thereof or a pharmaceutically acceptable salt of said compound or said prodrug.

Yet another aspect of this invention is directed to methods for treating osteotomy in a vertebrate, e.g., a mammal (including a human being), comprising administering to said vertebrate, e.g. a mammal having undergone an osteotomy, a bone restoration treating amount of a Formula I, II or III compound, a prodrug thereof or a pharmaceutically acceptable salt of said compound or said prodrug, wherein a bone restoration treating amount is an amount of said Formula I compound sufficient to restore bone in areas containing bone defects due to said osteotomy. In one aspect the Formula I, II or III compound, prodrug thereof or pharmaceutically acceptable salt of said compound or said prodrug is applied locally to a site of osteotomy.

Yet another aspect of this invention is directed to methods for treating alveolar or mandibular bone loss in a vertebrate, e.g., a mammal (including a human being), comprising administering to said vertebrate, e.g., a mammal suffering from an alveolar or mandibular bone loss, an alveolar or mandibular bone loss treating amount of a Formula I, II or III compound, a prodrug thereof or a pharmaceutically acceptable salt of said compound or said prodrug.

Yet another aspect of this invention is directed to methods for treating bone loss associated with periodontitis in a vertebrate, e.g., a mammal (including a human being), comprising administering to said vertebrate, e.g., mammal suffering from bone loss associated with periodontitis, a bone loss associated with periodontitis treating amount of a Formula I, II or III compound, a prodrug thereof or a pharmaceutically acceptable salt of said compound or said prodrug.

Yet another aspect of this invention is directed to methods for treating childhood idiopathic bone loss in a child comprising administering to said child suffering from childhood idiopathic bone loss, a childhood idiopathic bone loss treating amount of a Formula I, II or III compound, a prodrug thereof or a pharmaceutically acceptable salt of said compound or said prodrug.

Yet another aspect of this invention is directed to methods for treating "secondary osteoporosis", which includes glucocorticoid-induced osteoporosis, hyperthyroidism-induced osteoporosis, immobilization-induced osteoporosis, heparin-induced osteoporosis or immunosuppressive-induced osteoporosis in a vertebrate, e.g., a mammal (including a human being), by administering to said vertebrate, e.g., a mammal suffering from "secondary osteoporosis," a "secondary osteoporosis" treating amount of a Formula I, II or III compound, a prodrug thereof or a pharmaceutically acceptable salt of said compound or said prodrug.

Yet another aspect of this invention is directed to methods for treating glucocorticoid-induced osteoporosis in a vertebrate, e.g., a mammal (including a human being), comprising administering to said vertebrate, e.g., a mammal suffering from glucocorticoid-induced osteoporosis, a glucocorticoid-induced osteoporosis treating amount of a Formula I, II or III compound, a prodrug thereof or a pharmaceutically acceptable salt of said compound or said prodrug.

Yet another aspect of this invention is directed to methods for treating hyperthyroidism-induced osteoporosis in a vertebrate, e.g., a mammal (including a human being), comprising administering to said vertebrate, e.g., a mammal suffering from hyperthyroidism-induced osteoporosis, a hyperthyroidism-induced osteoporosis treating amount of a Formula I, II or III compound, a prodrug thereof or a pharmaceutically acceptable salt of said compound or said prodrug.

Yet another aspect of this invention is directed to methods for treating immobilization-induced osteoporosis in a vertebrate, e.g., a mammal (including a human being), comprising administering to said vertebrate, e.g., a mammal suffering from immobilization-induced osteoporosis, an immobilization-induced osteoporosis treating amount of a Formula I, II or III compound, a prodrug thereof or a pharmaceutically acceptable salt of said compound or said prodrug.

Yet another aspect of this invention is directed to methods for treating heparin-induced osteoporosis in a vertebrate, e.g., a mammal (including a human being), comprising administering to said vertebrate, e.g., a mammal suffering from heparin-induced osteoporosis, a heparin-induced osteoporosis treating amount of a Formula I, II or III compound, a prodrug thereof or a pharmaceutically acceptable salt of said compound or said prodrug.

Yet another aspect of this invention is directed to methods for treating immunosuppressive-induced osteoporosis in a vertebrate, e.g., a mammal (including a human being), comprising administering to said vertebrate, e.g., a mammal suffering from immunosuppressive-induced osteoporosis, an immunosuppressive-induced osteoporosis treating amount of a Formula I, II or III compound, a prodrug thereof or a pharmaceutically acceptable salt of said compound or said prodrug.

Yet another aspect of this invention is directed to methods for treating a bone fracture in a vertebrate, e.g., a mammal (including a human being), comprising administering to said vertebrate, e.g., a mammal suffering from a bone fracture, a bone fracture treating amount of a Formula I, II or III compound, a prodrug thereof or a pharmaceutically acceptable salt of said compound or said prodrug. In one aspect of this invention for treating a bone fracture the Formula I, II or III compound, prodrug thereof or pharmaceutically acceptable salt of said compound or said prodrug is applied locally to the site of bone fracture. In another aspect of this invention the Formula I, II or III compound, prodrug thereof or pharmaceutically acceptable salt of said compound or said prodrug is administered systemically.

Yet another aspect of this invention is directed to methods for enhancing bone healing following facial reconstruction, maxillary reconstruction or mandibular reconstruction in a vertebrate, e.g., a mammal (including a human being), comprising administering to said vertebrate, e.g., a mammal which has undergone facial reconstruction maxillary reconstruction or mandibular reconstruction, a bone enhancing amount of a Formula I, II or III compound, a prodrug thereof or a pharmaceutically acceptable salt of said compound or said prodrug. In one aspect of this method the Formula I, II or III compound, prodrug thereof or pharmaceutically acceptable salt of said compound or said prodrug is applied locally to the site of bone reconstruction.

Yet another aspect of this invention is directed to methods for treating prosthetic ingrowth in a vertebrate such as promoting bone ingrowth into a bone prosthesis in, e.g., a mammal (including a human being), comprising administering to said vertebrate, e.g., a mammal suffering from prosthetic ingrowth, a prosthetic ingrowth treating amount of a Formula I, II or III compound, a prodrug thereof or a pharmaceutically acceptable salt of said compound or said prodrug.

Yet another aspect of this invention is directed to methods for inducing vertebral synostosis in a vertebrate, e.g., a mammal (including a human being), comprising administering to said vertebrate, e.g., a mammal undergoing surgery for vertebral synostosis, a therapeutically effective amount of a Formula I, II or III compound, a prodrug thereof or a pharmaceutically acceptable salt of said compound or said prodrug.

Yet another aspect of this invention is directed to methods for enhancing long bone extension in a vertebrate, e.g., a mammal (including a human being), comprising administering to said vertebrate, e.g., a mammal suffering from an insufficiently sized long bone, a long bone enhancing amount of a Formula I, II or III compound, a prodrug thereof or a pharmaceutically acceptable salt of said compound or said prodrug.

Yet another aspect of this invention is directed to methods for strengthening a bone graft in a vertebrate, e.g., a mammal (including a human being), comprising administering to said vertebrate, e.g., a mammal in receipt of a bone graft, a bone graft strengthening amount of a Formula I, II or III compound, a prodrug thereof or a pharmaceutically acceptable salt of said compound or said prodrug. Additionally, a compound of Formula I, II or III, a prodrug thereof or a pharmaceutically acceptable salt of said compound or said prodrug can be used as an alternative to bone graft surgery. In one aspect of this method the Formula I, II or III compound, a prodrug thereof or a pharmaceutically acceptable salt of said compound or said prodrug is applied locally to the site of the bone graft. In another aspect of this method, a Formula I, II or III compound, a prodrug thereof or a pharamceutically acceptable salt of said compound or said prodrug is applied directly to the bone by injection or direct application to the bone surface.

A preferred dosage is about 0.001 to 100 mg/kg/day of the Formula I, II or III compound, prodrug thereof or pharmaceutically acceptable salt of said compound or said prodrug. An especially preferred dosage is about 0.01 to 10 mg/kg/day of the Formula I, II or III compound, prodrug thereof or pharmaceutically acceptable salt of said compound or said prodrug.

This invention is also directed to pharmaceutical compositions which comprise a therapeutically effective amount of a compound of Formula I, a prodrug thereof or a pharmaceutically acceptable salt of said compound or said prodrug and a pharmaceutically acceptable carrier or diluent.

This invention is also directed to pharmaceutical compositions for the augmentation of bone mass which comprise a bone mass augmenting amount of a compound of Formula I, a prodrug thereof or a pharmaceutically acceptable salt of said compound or said prodrug and a pharmaceutically acceptable carrier or diluent.

This invention is also directed to pharmaceutical compositions for the treatment of a condition which presents with low bone mass in a vertebrate, e.g., a mammal (including a human being), which comprise a low bone mass condition treating amount of a compound of Formula I, a prodrug thereof or a pharmaceutically acceptable salt of said compound or said prodrug and a pharmaceutically acceptable carrier or diluent.

This invention is also directed to pharmaceutical compositions for the treatment of osteoporosis, bone fractures, osteotomy, bone loss associated with periodontitis, or prosthetic ingrowth in a vertebrate, e.g., a mammal (including a human being), which comprises a therapeutically effective amount of a compound of Formula I, a prodrug thereof or a pharmaceutically acceptable salt of said compound or said prodrug and a pharmaceutically acceptable carrier or diluent.

This invention is also directed to pharmaceutical compositions for the treatment of "secondary osteoporosis," which includes glucocorticoid-induced osteoporosis, hyperthyroidism-induced osteoporosis, immobilization-induced osteoporosis, heparin-induced osteoporosis or immunosuppressive-induced osteoporosis in a vertebrate, e.g., a mammal (including a human being), which comprise a "secondary osteoporosis" treating amount of a compound of Formula I, a prodrug thereof or a pharmaceutically acceptable salt of said compound or said prodrug and a pharmaceutically acceptable carrier or diluent.

This invention is also directed to pharmaceutical compositions for the treatment of osteoporosis in a vertebrate, e.g., a mammal (including a human being), which comprise an osteoporosis treating amount of a compound of the Formula I, a prodrug thereof or a pharmaceutically acceptable salt of said compound or said prodrug and a pharmaceutically acceptable carrier or diluent.

This invention is also directed to pharmaceutical compositions for enhancing bone fracture healing in a vertebrate, e.g., a mammal (including a human being), which comprise a bone fracture treating amount of a compound of the Formula I a prodrug thereof or a pharmaceutically acceptable salt of said compound or said prodrug and a pharmaceutically acceptable carrier or diluent.

This invention is also directed to pharmaceutical compositions for the treatment of osteotomy in a vertebrate, e.g., a mammal (including a human being), comprising administering to said vertebrate, e.g. a mammal having undergone an osteotomy, a bone restoration treating amount of a Formula I compound, a prodrug thereof, or a pharmaceutically acceptable salt of said compound or said prodrug, wherein a bone restoration treating amount is an amount of said Formula I compound, prodrug thereof or pharmaceutically acceptable salt of said compound or said prodrug sufficient to restore bone in areas containing bone defects due to said osteotomy. In one aspect the Formula I compound, prodrug thereof or pharmaceutically acceptable salt of said compound or said prodrug is applied locally to an osteotomy site.

This invention is also directed to pharmaceutical compositions facilitating bone healing after an osteotomy in a vertebrate, e.g., a mammal (including a human being), comprising administering to said vertebrate, e.g., a mammal having undergone an osteotomy, a bone healing amount of a Formula I compound, a prodrug thereof or a pharmaceutically acceptable salt of said compound or said prodrug. In one aspect, the Formula I compound, prodrug or pharmaceutically acceptable salt of said compound or said prodrug is applied locally to an osteotomy site.

This invention is also directed to pharmaceutical compositions for the treatment of alveolar or mandibular bone loss in a vertebrate, e.g., a mammal (including a human being), which comprise an alveolar or mandibular bone loss treating amount of a compound of the Formula I, a prodrug thereof or a pharmaceutically acceptable salt of said compound or said prodrug and a pharmaceutically acceptable carrier or diluent.

This invention is also directed to pharmaceutical compositions for the treatment of childhood idiopathic bone loss in a child which comprise a childhood idiopathic bone loss treating amount of a compound of the Formula I, a prodrug thereof or a pharmaceutically acceptable salt of said compound or said prodrug and a pharmaceutically acceptable carrier or diluent.

This invention is also directed to pharmaceutical compositions for the augmentation of bone healing following facial reconstruction, maxillary reconstruction or mandibular reconstruction in a vertebrate, e.g., a mammal (including a human being), which comprise a bone healing amount of a compound of the Formula I, a prodrug thereof or a pharmaceutically acceptable salt of said compound or said prodrug and a pharmaceutically acceptable carrier or diluent.

This invention is also directed to pharmaceutical compositions for the treatment of bone loss associated with periodontitis in a vertebrate, e.g., a mammal (including a human being), which comprise a bone loss associated with periodontitis treating amount of a compound of the Formula I, a prodrug thereof or a pharmaceutically acceptable salt of said compound or said prodrug and a pharmaceutically acceptable carrier or diluent.

This invention is also directed to pharmaceutical compositions for the treatment of prosthetic ingrowth in a vertebrate, e.g., a mammal (including a human being), which comprise a prosthetic ingrowth treating amount of a compound of the Formula I, a prodrug thereof or a pharmaceutically acceptable salt of said compound or said prodrug and a pharmaceutically acceptable carrier or diluent This invention is also directed to pharmaceutical compositions for inducing vertebral synostosis in a vertebrate, e.g., a mammal (including a human being), which comprise a therapeutically effective amount of a compound of the Formula I, a prodrug thereof or a pharmaceutically acceptable salt of said compound or said prodrug and a pharmaceutically acceptable carrier or diluent.

This invention is also directed to pharmaceutical compositions for enhancing bone union in a long bone extension procedure in a vertebrate, e.g., a mammal (including a human being), which comprise a bone mass augmentation treating amount of a compound of the Formula I, a prodrug thereof or a pharmaceutically acceptable salt of said compound or said prodrug and a pharmaceutically acceptable carrier or diluent.

This invention is also directed to pharmaceutical compositions for the treatment of glucocorticoid-induced osteoporosis in a vertebrate, e.g., a mammal (including a human being), which comprise a glucocorticoid-induced osteoporosis treating amount of a compound of the Formula I, a prodrug thereof or a pharmaceutically acceptable salt of said compound or said prodrug and a pharmaceutically acceptable carrier or diluent.

This invention is also directed to pharmaceutical compositions for the treatment of hyperthyroidism-induced osteoporosis in a vertebrate, e.g., a mammal (including a human being), which comprise a hyperthyroidism-induced osteoporosis treating amount of a compound of the Formula I, prodrug thereof or a pharmaceutically acceptable salt of said compound or said prodrug and a pharmaceutically acceptable carrier or diluent.

This invention is also directed to pharmaceutical compositions for the treatment of immobilization-induced osteoporosis in a vertebrate, e.g., a mammal (including a human being), which comprise an immobilization-induced osteoporosis treating amount of a compound of the Formula I, a prodrug thereof or a pharmaceutically acceptable salt of said compound or said prodrug and a pharmaceutically acceptable carrier or diluent.

This invention is also directed to pharmaceutical compositions for the treatment of heparin-induced osteoporosis in a vertebrate, e.g., a mammal (including a human being) which comprise a heparin-induced osteoporosis treating amount of a compound of the Formula I, a prodrug thereof or a pharmaceutically acceptable salt of said compound or said prodrug and a pharmaceutically acceptable carrier or diluent.

This invention is also directed to pharmaceutical compositions for the treatment of immunosuppressive-induced osteoporosis in a vertebrate, e.g., a mammal (including a human being) which comprise an immunosuppressive-induced osteoporosis treating amount of a compound of the Formula I, a prodrug thereof or a pharmaceutically acceptable salt of said compound or said prodrug and a pharmaceutically acceptable carrier or diluent.

Yet another aspect of this invention is directed to combinations of the Formula I, II or III compounds a prodrug thereof or a pharmaceutically acceptable salt of said compound or said prodrug and other compounds as described below.

Yet another aspect of this invention is directed to pharmaceutical compositions comprising a compound of Formula I, a prodrug thereof or a pharmaceutically acceptable salt of said compound or said prodrug and an anti-resorptive agent, a prodrug thereof and a pharmaceutically acceptable salt of said agent or said prodrug and for the use of such compositions for the treatment or prevention of conditions which present with low bone mass, including osteoporosis in a vertebrates, e.g., mammals (e.g., humans, particularly women) or the use of such compositions for other bone mass augmenting uses.

The combinations of this invention comprise a therapeutically effective amount of a first compound, said first compound being a Formula I, II or III compound, a prodrug thereof or a pharmaceutically acceptable salt of said compound or said prodrug; and a therapeutically effective amount of a second compound, a prodrug of said second compound or a pharmaceutically acceptable salt of said second compound or said prodrug, said second compound being an anti-resorptive agent such as an estrogen agonist/antagonist or a bisphosphonate.

Another aspect of this invention is methods for treating vertebrates, e.g., mammals which present with low bone mass comprising administering to said vertebrate, e.g., a mammal having a condition which presents with low bone mass a. an amount of a first compound, said first compound being a Formula I, II or III compound, a prodrug thereof or a pharmaceutically acceptable salt of said compound or said prodrug; and b. an amount of a second compound, a prodrug thereof or a pharmaceutically acceptable salt of said second compound or said prodrug, said second compound being an anti-resorptive agent such as an estrogen agonist/antagonist or a bisphosphonate.

Such compositions and methods may also be used for other bone mass augmenting uses.

A preferred aspect of this method is wherein the condition which presents with low bone mass is osteoporosis.

Another preferred aspect of this method is wherein the first compound and the second compound are administered substantially simultaneously.

Another preferred aspect of this method is wherein the first compound is administered for a period of from about one week to about five years.

An especially preferred aspect of this method is wherein the first compound is administered for a period of from about one week to about three years.

Optionally the administration of the first compound is followed by administration of the second compound wherein the second compound is an estrogen agonist/antagonist for a period of from about three months to about three years without the administration of the first compound during the second period of from about three months to about three years.

Alternatively, the administration of the first compound is followed by administration of the second compound wherein the second compound is an estrogen agonist/antagonist for a period greater than about three years without the administration of the first compound during the greater than about three year period.

Another aspect of this invention is a kit comprising:

a. an amount of a Formula I, II or III compound, a prodrug thereof or a pharmaceutically acceptable salt of said compound or said prodrug and a pharmaceutically acceptable carrier or diluent in a first unit dosage form;

b. an amount of an anti-resorptive agent such as an estrogen agonist/antagonist or a bisphosphonate, a prodrug thereof or a pharmaceutically acceptable salt of said agent or said prodrug and a pharmaceutically acceptable carrier or diluent in a second unit dosage form; and c. container means for containing said first and second dosage forms.

Yet another aspect of this invention is directed to pharmaceutical compositions including a compound of Formula I, II or Ill, a prodrug thereof or a pharmaceutically acceptable salt of said compound or said prodrug and another bone anabolic agent (although the other bone anabolic agent may be a different Formula I, II or III compound) and for the use of such compositions for the treatment of conditions which present with low bone mass, including osteoporosis in vertebrates, e.g., mammals (e.g., humans, particularly women) or the use of such compositions for other bone mass augmenting uses.

The compositions comprise a therapeutically effective amount of a first compound, said first compound being a Formula I, II or III compound, a prodrug thereof or a pharmaceutically acceptable salt of said compound or said prodrug; and a therapeutically effective amount of a second compound, said second compound being another bone anabolic agent, a prodrug thereof or a pharmaceutically acceptable salt of said agent or said prodrug.

Another aspect of this invention is methods for treating vertebrates, e.g., mammals which present with low bone mass comprising administering to said vertebrate, e.g., a mammal having a condition which presents with low bone mass a. an amount of a first compound, said first compound being a Formula I, II or III compound, a prodrug thereof or a pharmaceutically acceptable salt of said compound or said prodrug; and b. an amount of a second compound, said second compound being another bone anabolic agent, a prodrug thereof or a pharmaceutically acceptable salt of said agent or said prodrug.

Such compositions and methods may also be used for other bone mass augmenting uses.

A preferred aspect of this method is wherein the condition which presents with low bone mass is osteoporosis.

Another preferred aspect of this method is wherein the first compound and the second compound are administered substantially simultaneously.

Another aspect of this invention is a kit comprising:

a. an amount of a Formula I, II or III compound, a prodrug thereof or a pharmaceutically acceptable salt of said compound or said prodrug and a pharmaceutically acceptable carrier or diluent in a first unit dosage form;

b. an amount of a second compound, said second compound being another bone anabolic agent, a prodrug thereof or a pharmaceutically acceptable salt of said agent or said prodrug and a pharmaceutically acceptable carrier or diluent in a second unit dosage form; and c. container means for containing said first and second dosage forms.

Where used in any of the above methods, kits and compositions, certain bone anabolic agents, estrogen agonists/antagonists and bisphosphonates are preferred or especially preferred.

Preferred bone anabolic agents include IGF-1, bone morphogenetic protein (BMP), prostaglandins, prostaglandin agonists/antagonists, sodium fluoride, parathyroid hormone (PTH), active fragments of parathyroid hormone, parathyroid hormone related peptides and active fragments and analogues of parathyroid hormone related peptides, growth hormones or growth hormone secretagogues and the pharmaceutically acceptable salts thereof.

Preferred estrogen agonists/antagonists include droloxifene, raloxifene, tamoxifen; 4-hydroxy-tamoxifen; toremifene; centchroman;levormeloxifene; idoxifene;

6-(4-hydroxy-phenyl)-5-[4-(2-piperidin-1-yl-ethoxy) benzyl]-naphthalen-2-ol;

{4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone;

3-(4-(1,2-diphenyl-but-1-enyl)-phenyl)-acrylic acid;

2-(4-methoxy-phenyl)-3-[4-(2-piperidin-1-yl-ethoxy)-phenoxy]benzo[b]thiophen-6-ol;

cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydronaphthalene-2-ol;

cis-6-phenyl-5-[4-(2-pyrrolidin-1-yl-ethoxy)-phenyl]-5,6,7,8-tetrahydronaphthalene-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol;

1-(4'-pyrrolidinolethoxyphenyl)-2-phenyl-6-hydroxy-1,2,3,4-tetrahydroisoquinoline; and the pharmaceutically acceptable salts thereof.

Especially preferred estrogen agonists/antagonists include droloxifene;

3-(4-(1,2-diphenyl-but-1-enyl)-phenyl)-acrylic acid;

2-(4-methoxy-phenyl)-3-[4-(2-piperidin-1-yl-ethoxy)-phenoxy]benzo[b]thiophen-6-ol;

cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydronaphthalene-2-ol;

cis-1-[6'-pyrrolodinoethoxy-3'-pyridyl]-2-phenyl-6-hydroxy-1,2,3,4-tetrahydro-naphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol;

1-(4'-pyrrolidinolethoxyphenyl)-2-phenyl-6-hydroxy-1,2,3,4-tetrahydroisoquinoline; and the pharmaceutically acceptable salts thereof.

Preferred bisphosphonates include, tiludronic acid, alendronic acid, zoledronic acid, ibandronic acid, risedronic acid, etidronic acid, clodronic acid, pamidronic acid and their pharmaceutically acceptable salts.

It will be recognized that prodrugs and pharmaceutically acceptable salts may be formed from the compounds used as the second compounds in the combinations of this invention. All of such prodrugs and pharmaceutically acceptable salts so formed are within the scope of this invention. Particularly preferred salt forms include droloxifene citrate, raloxifene hydrochloride, tamoxifen citrate and toremifen citrate.

The phrase "condition(s) which presents with low bone mass" refers to a condition where the level of bone mass is below the age specific normal as defined in standards by the World Health Organization "Assessment of Fracture Risk and its Application to Screening for Postmenopausal Osteoporosis (1994). Report of a World Health Organization Study Group. World Health Organization Technical Series 843". Included in "condition(s) which presents with low bone mass" are primary and secondary osteoporosis. Secondary osteoporosis includes glucocorticoid-induced osteoporosis, hyperthyroidism-induced osteoporosis, immobilization-induced osteoporosis, heparin-induced osteoporosis and immunosuppressive-induced osteoporosis. Also included is periodontal disease, alveolar bone loss, osteotomy bone loss and childhood idiopathic bone loss. The phrase "condition(s) which presents with low bone mass" also includes long term complications of osteoporosis such as curvature of the spine, loss of height and prosthetic surgery.

The phrase "condition which presents with low bone mass" also refers to said vertebrate, e.g., a mammal known to have a significantly higher than average chance of developing such diseases as are described above including osteoporosis (e.g., post-menopausal women, men over the age of 60).

Other bone mass augmenting or enhancing uses include bone restoration, increasing the bone fracture healing rate, enhancing the rate of successful bone grafts, bone healing following facial reconstruction or maxillary reconstruction or mandibular reconstruction, prosthetic ingrowth, vertebral synostosis or long bone extension.

The compounds and compositions of this invention may also be used in conjunction with orthopedic devices such as spinal fusion cages, spinal fusion hardware, internal and external bone fixation devices, screws and pins.

Those skilled in the art will recognize that the term bone mass actually refers to bone mass per unit area which is sometimes (although not strictly correctly) referred to as bone mineral density.

The term "treating", "treat" or "treatment" as used herein includes preventative (e.g., prophylactic) and palliative and curative treatment.

By "pharmaceutically acceptable" it is meant the carrier or diluent, diluent, excipients, and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I, II or III compounds include but are not limited to substituents wherein the R moiety in Formula I or II and the $R^8$ moiety in Formula III is independently carboxyl and the free hydrogen is replaced by $(C_1-C_4)$alkyl, $(C_2-C_7)$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as b-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Exemplary five to six membered aromatic rings optionally having one or two heteroatoms selected independently from oxygen, nitrogen and sulfur are phenyl, furyl, thienyl, pyrrolyl, oxazolyl, thiazolyl, imidazolyl, pyrazolyl, isoxazolyl, isothiazolyl, pyridyl, pyridiazinyl, pyrimidinyl and pyrazinyl.

Exemplary partially saturated, fully saturated or fully unsaturated five to eight membered rings optionally having one to four heteroatoms selected independently from oxygen, sulfur and nitrogen (i.e., Ar, $Ar^1$ and $Ar^2$) are cyclopentyl, cyclohexyl, cycloheptyl, cyclooctyl and phenyl. Further exemplary five membered rings are furyl, thienyl, 2H-pyrrolyl, 3H-pyrrolyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings are 2H-pyranyl, 4H-pyranyl, pyridyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl.

Further exemplary seven membered rings are azepinyl, oxepinyl, thiepinyl and 1,2,4-diazepinyl.

Further exemplary eight membered rings are cyclooctyl, cyclooctenyl and cyclooctadienyl.

Exemplary bicyclic rings consisting of two fused independently partially saturated, fully saturated or fully unsaturated five and/or six membered rings, taken independently, optionally having one to four heteroatoms selected independently from nitrogen, sulfur and oxygen are indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, 4H-quinolizinyl, quinolinyl, isoquinotinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, 1,4-benzodioxan, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

Exemplary tricyclic rings consisting of three fused independently partially saturated, fully saturated or fully unsaturated five and/or six membered rings, taken independently, optionally having one to four heteroatoms selected independently from nitrogen, sulfur and oxygen are indacenyl, biphenylenyl, acenaphthylenyl, fluorenyl, phenalenyl, phenanthrenyl, anthracenyl, naphthothienyl, thianthrenyl, xanthenyl, phenoxathiinyl, carbazolyl, carbolinyl, phenanthridinyl, acridinyl, perimidinyl, phenanthrolinyl, phenazinyl, phenothiazinyl and phenoxazinyl. It will be understood that the fully saturated and all partially unsaturated forms of these rings are within the scope of this invention. Further, it will be understood that the heteroatom or heteroatoms in the heterocyclic rings can be substituted at any non-bridgehead position within said ring.

By alkylene is meant saturated hydrocarbon (straight chain or branched) wherein a hydrogen atom is removed from each of the terminal carbons. Exemplary of such groups (assuming the designated length encompasses the particular example) are methylene, ethylene, propylene, butylene, pentylene, hexylene and heptylene.

By alkenylene is meant a hydrocarbon containing monounsaturation in the form of one double bond wherein said hydrocarbon is a straight chain or branched and wherein a hydrogen atom is removed from each of the terminal carbons. Exemplary of such groups (assuming the designated length encompasses the particular example) are ethenylene (or vinylene), propenylene, butenylene, pentenylene, hexenylene and heptenylene.

By alkynylene is meant a hydrocarbon containing di-unsaturation in the form of one triple bond wherein said hydrocarbon is a straight chain or branched and wherein a hydrogen atom is removed from each of the terminal carbons. Exemplary of such groups (assuming the designated length encompasses the particular example) are ethynylene, propynylene, butynylene, pentynylene, hexynylene and heptynylene.

By halo is meant chloro, bromo, iodo, or fluoro.

By alkyl is meant a straight chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant a straight chain saturated alkyl or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein, the term mono-N- or di-N,N-($C_1$–$C_x$) alkyl . . . refers to the ($C_1$–$C_x$)alkyl moiety taken independently when it is di-N,N-($C_1$–$C_x$)alkyl . . . (x refers to integers and is taken independently when two ($C_1$–$C_x$)alkyl groups are present, e.g., methylethylamino is within the scope of di-N,N-($C_1$–$C_x$)alkyl).

It is to be understood that if a carbocyclic or heterocyclic moiety may be bonded or otherwise attached to a designated substrate, through differing ring atoms without denoting a specific point of attachment, then all possible points are intended, whether through a carbon atom or, for example, a trivalent nitrogen atom For example, the term "pyridyl" means 2-, 3-, or 4-pyridyl, the term "thienyl" means 2-, or 3-thienyl, and so forth.

The expression "pharmaceutically acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction inert solvent" and "inert solvent" refers to a solvent which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers such as enantiomers and diastereomers; and configurational isomers such as cis and trans olefins and cis and trans substitution patterns on saturated alicyclic rings. All such isomers and mixtures thereof are included in this invention.

Hydrates and solvates of the compounds of this invention are also included.

The methods and compounds of this invention result in bone formation resulting in decreased fracture rates. This invention makes a significant contribution to the art by providing compounds and methods that increase bone formation resulting in prevention, retardation, and/or regression of osteoporosis and related bone disorders.

Other features and advantages will be apparent from the specification and claims which describe the invention.

DETAILED DESCRIPTION OF THE INVENTION

In general the compounds of this invention can be made by processes which include processes well known in the chemical arts.

Compounds of the formula I

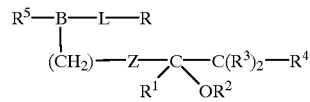

wherein B, L, R, $R^1$, $R^2$, $R^3$, $R^4$, $R^5$ and Z are as defined above are prepared using methods analagous to the methods disclosed in U.S. Pat. Nos. 3,987,091; 3,991,087; 4,033,996; and 4,066,692, each of which is incorporated herein by reference.

Compounds of the formula II

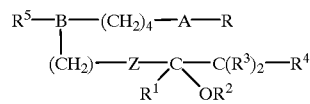

wherein

A is ethylene, n-propylene, α-methylethylene, β-methylethylene, α,α-dimethylethylene, β,β-dimethylethylene or oxymethylene;

B is N;

R is carboxy, ($C_1$–$C_{10}$)alkanoyloxy, carbamoyl or mono-N- or di-N,N-($C_1$–$C_4$)alkyl-substituted carbamoyl;

$R^1$ is H;

$R^2$ is H or ($C_2$–$C_5$) alkanoyl;

$R^3$ is independently H or methyl;

$R^4$ is H, ($C_1$–$C_4$) alkyl, vinyl or 2,2,2-trifluoroethyl;

$R^5$ is formyl, acetyl, propionyl, acryloyl, hydroxyacetyl or 2,2,2-trifluoroethyl; and Z is ethylene, vinylene or ethynylene are prepared as described in U.S. Pat. No. 3,987,091, which is incorporated herein by reference.

Compounds of the formula II $$R^5\text{—B—}(CH_2)_4\text{—A—R}$$
$$(CH_2)\text{—Z—}\underset{R^1}{C}\text{—}\underset{OR^2}{C(R^3)_2}\text{—R}^4$$

wherein

A is ethylene, n-propylene, α-methylethylene, β-methylethylene, α,α-dimethylethylene, β,β-dimethylethylene or oxymethylene;

B is C(Q);

R is carboxy, $(C_1–C_{10})$alkanoyloxy, carbamoyl or mono-N- or di-N,N-$(C_1–C_4)$alkyl-substituted carbamoyl;

$R^1$ is hydrogen or methyl;

$R^2$ is H or $(C_2–C_5)$alkanoyl;

$R^3$ is independently H or methyl;

$R^4$ is H, $(C_1–C_4)$ alkyl, vinyl or 2,2,2-trifluoroethyl; or $R^4$ and $R^1$ are taken together to form a 5–9 membered carbocyclic ring;

$R^5$ is acetyl;

Q is chloro, bromo, methyl, phenyl or substituted phenyl; and

Z is ethylene are prepared as disclosed in U.S. Pat. No. 3,991,087, which is incorporated herein by reference.

Compounds of the formula II $$R^5\text{—B—}(CH_2)_4\text{—A—R}$$
$$(CH_2)\text{—Z—}\underset{R^1}{C}\text{—}\underset{OR^2}{C(R^3)_2}\text{—R}^4$$

wherein

A is ethylene, n-propylene, α-methylethylene, β-methylethylene, α,α-dimethylethylene, β,β-dimethylethylene or oxymethylene;

B is N;

R is carboxy, $(C_1–C_{10})$ alkoxycarbonyl, carbamoyl, mono-N- or di-N,N-$(C_1–C_4)$alkyl-substituted carbamoyl or —COOY wherein Y is 1-succinimidoethyl, 1-pivaloyloxyethyl, 2-acetamidoethyl or diloweralkylaminoloweralkyl;

$R^1$ is H, methyl, ethyl or propyl;

$R^2$ is H or $(C_2–C_5)$ alkanoyl;

$R^3$ is independently H or methyl;

$R^4$ is H, $(C_1–C_4)$ alkyl, vinyl or 2,2,2-trifluoroethyl; or $R^4$ and $R^1$ are taken together to form a 5–9 membered carbocyclic ring;

$R^5$ is $R^6SOy$;

Z is ethylene, vinylene or ethynylene;

$R^6$ is methyl, ethyl, propyl or isopropyl; and y is 1 or 2 are prepared as disclosed in U.S. Pat. No. 4,033,996, which is incorporated herein by reference.

Compounds of the formula II $$R^5\text{—B—}(CH_2)_4\text{—A—R}$$
$$(CH_2)\text{—Z—}\underset{R^1}{C}\text{—}\underset{OR^2}{C(R^3)_2}\text{—R}^4$$

wherein

A is ethylene, n-propylene, α-methylethylene, β-methylethylene, α,α-dimethylethylene, β,β-dimethylethylene or oxymethylene;

B is C(Q);

R is carboxy, $(C_1–C_{10})$ alkoxycarbonyl, carbamoyl, mono-N- or di-N,N-$(C_1–C_4)$alkyl-substituted carbamoyl or —COOY wherein Y is 1-succinimidoethyl, 1-pivaloyloxyethyl, 2-acetamidoethyl; diloweralkylaminoloweralkyl; or carbazoyl;

$R^1$ is H or methyl;

$R^2$ is H or $(C_2–C_5)$ alkanoyl;

$R^3$ is independently H or methyl;

$R^4$ is H, $(C_1–C_4)$ alkyl, vinyl or 2,2,2-trifluoroethyl; or $R^4$ and $R^1$ are taken together to form a 5–9 membered carbocyclic ring;

$R^5$, when B is C(Q), is formyl, acetyl, pivaloyl, propionyl, acryloyl, hydroxyacetyl, 3-hydroxypropionyl, hydroxymethyl, 1-hydroxyethyl, 1,2-dihydroxyethyl, 1,3-dihydroxypropyl or 1-hydroxyl-1-methylethyl;

Q is H; and

Z is methylene, ethylene, n-propylene, tetramethylene, vinylene or ethynylene are prepared as disclosed in U.S. Pat. No. 4,066,692, which is incorporated herein by reference.

Compounds of the formula III $$R^7SO_2\text{—N—X—}\underset{}{\bigcirc}\text{—G—R}^8$$
$$CH_2\text{—L—}\underset{R^9}{C}\text{—}\underset{OH}{C(R^{10})_2}\text{—R}^{11}$$

wherein $R^7$ is $(C_1–C_4)$ alkyl;

$R^8$ is carboxy or $(C_1–C_{10})$ alkoxycarbonyl;

$R^9$ is H or methyl;

$R^{10}$ is independently H or methyl;

$R^{11}$ is $(C_3–C_6)$ alkyl; or $R^{11}$ and $R^9$ are taken together to form a 5–9 membered carbocyclic ring;

G is $(CH_2)_n$, oxymethylene or vinylene;

X is $(CH_2)_m$;

L is ethylene, vinylene or ethynylene;

n is 0 or 2; and

M is 1, 3 or 4; provided that the sum of chain-forming elements in G and X is limited to either 3 or 4 are prepared as disclosed in U.S. Pat. No. 4,112,236, which is incorporated herein by reference.

Compounds of the formula $NH_2$—L—R can be prepared according to methods well known to those skilled in the art, e.g., as set forth in U.S. Pat. No. 3,987,091 or as set forth in Preparations 2, 2a, 4, 5 and 7 below. Compounds of the formula $R^5$—NH—L—R are prepared according to methods well known to those skilled in the art, e.g., see Preparations 3, 6 and 8–11. Particularly compounds of the formula $R^5$—NH—L—R are prepared by reacting the corresponding amine with the appropriate carboxylic acid anhydride, carboxylic acid chloride or sulfonyl chloride in the presence of a mild base such as triethylamine, N,N-diisopropylamine or pyridine or by reacting the amine with a carboxylic acid in the presence of a suitable activating agent, to obtain the corresponding amido or sulfonamido compounds. Suitable activating agents are dicyclohexylcarbodiimide or carbonyl diimidazole.

It will be recognized that the compounds of Formula I of this invention and the compounds of Formulas II and III used in the methods of this invention can exist in radiolabelled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3H$, $^{14}C$, $^{32}P$, $^{35}S$, $^{18}F$ and $^{36}Cl$, respectively. Compounds of Formula I of this invention and compounds of Formulas II and III used in the methods of this invention which contain such radioisotopes and/or other radioisotopes of other atoms are within the scope of this invention. Tritiated, i.e., $^3H$, and carbon-14, i.e., $^{14}C$, radioisotopes are particularly preferred for their ease of preparation and detectability. Radiolabelled compounds of Formula I of this invention and radiolabelled compounds of Formulas II and III used in the methods of this invention can generally be prepared according to methods well known to those skilled in the art. Conveniently, such radiolabelled compounds can be prepared by carrying out the procedures disclosed herein or referenced hereby by substituting a readily available radiolabelled reagent for a non-radiolabelled reagent.

Those skilled in the art will recognize that anti-resorptive agents (for example progestins, polyphosphonates, bisphosphonate(s), estrogen agonists/antagonists, estrogen, estrogeniprogestin combinations, Premarin®, estrone, estriol or 17α- or 17β-ethynyl estradiol) may be used in conjunction with the compounds of this invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol.

Preferred progestins are medroxyprogestrone, norethindrone and norethynodrel.

Exemplary bone resorption inhibiting polyphosphonates include polyphosphonates of the type disclosed in U.S. Pat. No. 3,683,080, the disclosure of which is incorporated herein by reference. Preferred polyphosphonates are geminal diphosphonates (also referred to as bis-phosphonates). Tiludronate disodium is an especially preferred polyphosphonate. Ibandronic acid is an especially preferred polyphosphonate. Alendronate is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art according to standard assays including estrogen receptor binding assays, standard bone histomorphometric and densitometer methods, and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below.

A preferred estrogen agonist/antagonist is droloxifene: (phenol, 3-[1-[4[2-(dimethylamino)ethoxy]phenyl]-2-phenyl-1-butenyl]-, (E)-) and related compounds which are disclosed in U.S. Pat. No. 5,047,431, the disclosure of which is incorporated herein by reference.

Another preferred estrogen agonist/antagonist is tamoxifen: (ethanamine,2[-4-(1,2-diphenyl-1-butenyl)phenoxy]-N,N-dimethyl, (Z)-2-, 2-hydroxy-1,2,3-propanetricarboxylate(1:1)) and related compounds which are disclosed in U.S. Pat. No. 4,536,516, the disclosure of which is incorporated herein by reference.

Another related compound is 4-hydroxy tamoxifen which is disclosed in U.S. Pat. No. 4,623,660, the disclosure of which is incorporated herein by reference.

A preferred estrogen agonist/antagonist is raloxifene: (methanone, [6-hydroxy-2-(4-hydroxyphenyl)benzo[b]thien-3-yl][4-[2-(1-piperidinyl)ethoxy]phenyl] hydrochloride) which is disclosed in U.S. Pat. No. 4,418,068, the disclosure of which is incorporated herein by reference.

Another preferred estrogen agonist/antagonist is toremifene: (ethanamine, 2-[4-(4-chloro-1,2-diphenyl-1-butenyl)phenoxy]-N,N-dimethyl-, (Z-, 2-hydroxy-1,2,3-propanetricarboxylate (1:1) which is disclosed in U.S. Pat. No. 4,996,225, the disclosure of which is incorporated herein by reference.

Another preferred estrogen agonist/antagonist is 3-(4-(1, 2-diphenyl-but-1-enyl)-phenyl)-acrylic acid, which is disclosed in Willson et al., Endocrinology, 1997, 138, 3901–3911.

Another preferred estrogen agonist/antagonist is centchroman: 1-[2-[[4-(-methoxy-2,2, dimethyl-3-phenyl-chroman4-yl)-phenoxy]-ethyl]-pyrrolidine, which is disclosed in U.S. Pat. No. 3,822,287, the disclosure of which is incorporated herein by reference. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155, the disclosure of which is incorporated herein by reference.

Another preferred estrogen agonist/antagonist is 6-(4-hydroxy-phenyl)-5-[4-(2-piperidin-1-yl-ethoxy)-benzyl]-naphthalen-2-ol which is disclosed in U.S. Pat. No. 5,484,795, the disclosure of which is incorporated herein by reference.

Another preferred estrogen agonist/antagonist is 2-(4-methoxy-phenyl)-3-(4-(2-piperidin-1-yl-ethoxy)-phenoxy)-benzo[b]thiophen-6-ol which is disclosed in U.S. Pat. No. 5,488,058, the disclosure of which is incorporated herein by reference.

Another preferred estrogen agonist/antagonist is {4-[2-(2-aza-bicyclo[2.2.1]hept-2-yl)-ethoxy]-phenyl}-[6-hydroxy-2-(4-hydroxy-phenyl)benzo[b]thiophen- 3-yl]-methanone which is disclosed, along with methods of preparation, in PCT publication no. WO 95/10513 assigned to Pfizer Inc.

Other preferred estrogen agonist/antagonists include compounds as described in commonly assigned U.S. Pat. No. 5,552,412, the disclosure of which is incorporated herein by reference. Especially preferred compounds described therein are:

cis-6-(4-fluoro-phenyl)-5-[4-(2-piperidin-1-yl-ethoxy)-phenyl]-5,6,7,8-tetrahydro-naphthalene-2-ol;

(-)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is incorporated herein by reference). U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study World Health Organization, "Assessment of Fracture Risk and its Application to Screening for Postmenopausal Osteoporosis (1994). Report of a WHO Study Group. World Health Organization Technical Series 843."

Any prostaglandin, or prostaglandin agonist/antagonist may be used as the second compound in certain aspects of this invention. This includes utilizing two different compounds of Formula I, II or III of this invention. Those skilled in the art will recognize that IGF-1, sodium fluoride, bone morphogenetic proteins (BMPs), parathyroid hormone (PTH), active fragments of parathyroid hormone, growth hormone or growth hormone secretagogues may also be used. The following paragraphs describe exemplary second compounds of this invention in greater detail.

Any prostaglandin may be used as the second compound in certain aspects of this invention. The term prostaglandin refers to compounds which are analogs of the natural prostaglandins $PGD_1$, $PGD_2$, $PGE_2$, $PGE_1$ and $PGF_2$ which are useful in the treatment of osteoporosis. These compounds bind to the prostaglandin receptors. Such binding is readily determined by those skilled in the art according to standard assays (e.g., An S. et al., Cloning and Expression of the $EP_2$ Subtype of Human Receptors for Prostaglandin $E_2$, Biochemical and Biophysical Research Communications, 1993, 197(1):263–270).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$–$C_{14}$ and a cis double bond at the $C_5$–$C_6$ position.

A variety of prostaglandins are described and referenced below. However, other prostaglandins will be known to those skilled in the art. Exemplary prostaglandins are disclosed in U.S. Pat. Nos. 4,171,331 and 3,927,197, the disclosures of each of which are incorporated herein by reference.

Norrdin et al., *The Role of Prostaglandins in Bone In Vivo*, Prostaglandins Leukotriene Essential Fatty Acids 41,139–150, 1990 is a review of bone anabolic prostaglandins.

Any prostaglandin agonist/antagonist may be used as the second compound in certain aspects of this invention. The term prostaglandin agonist/antagonist refers to compounds which bind to prostaglandin receptors (e.g., An S. et al., Cloning and Expression of the $EP_2$ Subtype of Human Receptors for Prostaglandin $E_2$, Biochemical and Biophysical Research Communications, 1993, 197(1):263–270) and mimic the action of prostaglandin in vivo (e.g., stimulate bone formation and increase bone mass). Such actions are readily determined by those skilled in the art according to standard assays. Eriksen E. F. et al., *Bone Histomorphometry*, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296. A variety of these compounds are described and referenced below. However, other prostaglandin agonists/antagonists will be known to those skilled in the art. Exemplary prostaglandin agonists/antagonists are disclosed as follows.

Commonly assigned U.S. Pat. No. 3,932,389, the disclosure of which is incorporated herein by reference, discloses 2-descarboxy-2-(tetrazol-5-yl)-11-desoxy-15-substituted-omega-pentanorprostaglandins useful for bone formation activity.

Commonly assigned U.S. Pat. No. 4,018,892, the disclosure of which is incorporated herein by reference, discloses 16-aryl-13,14-dihydro-$PGE_2$ p-biphenyl esters useful for bone formation activity.

Commonly assigned U.S. Pat. No. 4,219,483, the disclosure of which is incorporated herein by reference, discloses 2,3,6-substituted-4-pyrones useful for bone formation activity.

Commonly assigned U.S. Pat. No. 4,132,847, the disclosure of which is incorporated herein by reference, discloses 2,3,6-substituted-4-pyrones useful for bone formation activity.

U.S. Pat. No. 4,000,309, the disclosure of which is incorporated herein by reference, discloses 16-aryl-13,14-dihydro-PGE$_2$ p-biphenyl esters useful for bone formation activity.

U.S. Pat. No. 3,982,016, the disclosure of which is incorporated herein by reference, discloses 16-aryl-13,14-dihydro-PGE$_2$ p-biphenyl esters useful for bone formation activity.

U.S. Pat. No. 4,621,100, the disclosure of which is incorporated herein by reference, discloses substituted cyclopentanes useful for bone formation activity.

U.S. Pat. No. 5,216,183, the disclosure of which is incorporated herein by reference, discloses cyclopentanones useful for bone formation activity.

Sodium fluoride may be used as the second compound in certain aspects of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478, the disclosure of which is incorporated herein by reference. The activity of sodium fluoride is readily determined by those skilled in the art according to biological protocols (e.g., see Eriksen E. F. et al., *Bone Histomorphometry*, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296).

Bone morphogenetic protein may be used as the second compound in certain aspects of this invention (e.g., see Ono, et al., Promotion of the Osteogenetic Activity of Recombinant Human Bone Morphogenetic Protein by Prostaglandin E1, *Bone*, 1996,19(6), 581–588).

Any parathyroid hormone (PTH) may be used as the second compound in certain aspects of this invention. The term parathyroid hormone refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication no. WO 94/01460). Such bone anabolic functional activity is readily determined by those skilled in the art according to standard assays (e.g., see Eriksen E. F. et al., Bone Histomorphometry, Raven Press, New York, 1994, pages 1–74; Grier S. J. et al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below. However, other parathyroid hormones will be known to those skilled in the art. Exemplary parathyroid hormones are disclosed in the following references.

"Human Parathyroid Peptide Treatment of Vertebral Osteoporosis", Osteoporosis Int., 3, (Supp 1):199–203.

"PTH 1-34 Treatment of Osteoporosis with Added Hormone Replacement Therapy: Biochemical, Kinetic and Histological Responses" Osteoporosis Int. 1:162–170.

Any growth hormone or growth hormone secretagogue may be used as the second compound in certain aspects of this invention. The term growth hormone secretagogue refers to a compound which stimulates the release of growth hormone or mimics the action of growth hormone (e.g., increases bone formation leading to increased bone mass). Such actions are readily determined by those skilled in the art according to standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art.

In particular a preferred growth hormone secretagogue is N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-677.

Other preferred growth hormone secretagogues include:
2-amino-N-[2-(3a-(R)-benzyl-2-methyl-3-oxo-2,3,3a,4,6,7-hexahydro-pyrazo-[4,3-c]pyridin-5-yl)-1-(R)-benzyloxymethyl-2-oxo-ethyl]-isobutyramide or its L-tartaric acid salt;

2-amino-N-{1-(R)-benzyloxymethyl-2-[3a-(R)-(4-fluoro-benzyl)-2-methyl-3-oxo-2,3,3a,4,6,7-hexahydro-pyrazolo[4,3-c]pyridin-5-yl]-2-oxo-ethyl}isobutyramide;

2-amino-N-[2-(3a-(R)-benzyl-3-oxo-2,3,3a,4,6,7-hexahydro-pyrazolo[4,3-c]pyridin-5-yl)-1-(R) benzyloxymethyl-2-oxo-ethyl]isobutyramide; and 2-amino-N-{1-(2,4-difluoro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide.

Some of the preparation methods useful for the preparation of the compounds described herein may require protection of remote functionality (e.g., primary amine, secondary amine, carboxyl in Formula I, II and III precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

The starting materials and reagents for the above described compounds are also readily available or can be easily synthesized by those skilled in the art using conventional methods of organic synthesis. For example, many of the compounds used herein are related to, or are derived from, compounds found in nature, in which there is a large scientific interest and commercial need, and accordingly many such compounds are commercially available or are reported in the literature or are easily prepared from other commonly available substances by methods which are reported in the literature. Such compounds include, for example, prostaglandins.

It will be recognized by persons skilled in the art that some of the compounds of this invention have at least one asymmetric carbon atom and therefore are enantiomers or diastereomers. Diasteromeric mixtures can be separated into their individual diastereomers on the basis of their physicochemical differences by methods known per se, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing, including both chemical hydrolysis methods and microbial lipase hydrolysis methods, e.g., enzyme catalyzed hydrolysis) the individual diastereomers to the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

Many of the compounds of this invention, including the compounds of Formulas I and II, the anti-resorptive agents, bone anabolic agents, prostaglandin agonists/antagonists, parathyroid hormones, growth hormones and growth hormone secretagogues, and prodrugs thereof, are acidic and they form a salt with a pharmaceutically acceptable cation. Some of the compounds of this invention, including the compounds of Formulas I and II, the anti-resorptive agents, bone anabolic agents, prostaglandin agonists/antagonists, parathyroid hormones, growth hormones and growth hormone secretagogues, and prodrugs thereof, are basic and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention, including the compounds of Formulas I and II, the anti-resorptive agents, bone anabolic agents, prostaglandin agonists/antagonists, parathyroid hormones, growth hormones and growth hormone secretagogues, form hydrates or solvates they are also within the scope of the invention.

In addition, all prodrugs of the compounds of this invention, including the compounds of Formulas I, II and III, the anti-resorptive agents, bone anabolic agents, prostaglandin agonists/antagonists, parathyroid hormones, growth hormones and growth hormone secretagogues, are within the scope of this invention. Further, many of the prodrugs of the compounds of this invention, including the compounds of Formulas I, II and III, the anti-resorptive agents, bone anabolic agents, prostaglandin agonists/antagonists, parathyroid hormones, growth hormones and growth hormone secretagogues can be converted to their pharmaceutically acceptable salts by methods described above for the compounds of this invention.

The compounds of this invention are all adapted to therapeutic use as agents that stimulate bone formation and increase bone mass in a vertebrates, e.g., mammals, and particularly humans. Since bone formation is closely related to the development of osteoporosis and bone related disorders, these compounds, by virtue of their action on bone, prevent, arrest and/or regress osteoporosis.

The utility of the compounds of the present invention as medical agents in the treatment of conditions which present with low bone mass (e.g., osteoporosis) in a vertebrates, e.g., mammals (e.g. humans, particularly the female) is demonstrated by the activity of the compounds of this invention in conventional assays, including an in vivo assay, a receptor binding assay, a cyclic AMP assay and the fracture healing assay (all of which are described below). The in vivo assay (with appropriate modifications within the skill in the art) may be used to determine the activity of other anabolic agents as well as the prostaglandin agonists of this invention. The estrogen agonist/antagonist protocol may be used to determine the activity of estrogen agonists/antagonists in particular and also other anti-resorptive agents (with appropriate modifications within the skill in the art). The combination and sequential treatment protocol described below is useful for demonstrating the utility of the combinations of the anabolic agents (e.g., the compounds of this invention) and anti-resorptive agents (e.g., estrogen agonists/antagonists) described herein. Such assays also provide a means whereby the activities of the compounds of this invention (or the other anabolic agents and anti-resorptive agents described herein) can be compared to each other and with the activities of other known compounds. The results of these comparisons are useful for determining dosage levels in a vertebrates, e.g., mammals, including humans, for the treatment of such diseases.

Anabolic Agent In Vivo Assay

The activity of anabolic bone agents in stimulating bone formation and increasing bone mass can be tested in intact male or female rats, sex hormone deficient male (orchidectomy) or female (ovariectomy) rats.

Male or female rats at different ages (such as 3 months of age) can be used in the study. The rats are either intact or castrated (ovariectomized or orchidectomized), and subcutaneously injected or gavaged with prostaglandin agonists at different doses (such as 1, 3, or 10 mg/kg/day) for 30 days. In the castrated rats, treatment is started at the next day after surgery (for the purpose of preventing bone loss) or at the time bone loss has already occured (for the purpose of restoring bone mass). During the study, all rats are allowed free access to water and a pelleted commercial diet (Teklad Rodent Diet #8064, Harlan Teklad, Madison, Wis.) containing 1.46% calcium, 0.99% phosphorus and 4.96 IU/g of Vitamin $D_3$. All rats are given subcutaneous injections of 10 mg/kg calcein on days 12 and 2 before sacrifice. The rats are sacrificed. The following endpoints are determined:

Femoral Bone Mineral Measurements:

The right femur from each rat is removed at autopsy and scanned using dual energy X-ray absorptiometry (DXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Tibial Bone Histomorphometric Analyses:

The right tibia is removed at autopsy, dissected free of muscle, and cut into three parts. The proximal tibia and the tibial shaft are fixed in 70% ethanol, dehydrated in graded concentrations of ethanol, defatted in acetone, then embedded in methyl methacrylate (Eastman Organic Chemicals, Rochester, N.Y.).

Frontal sections of proximal tibial metaphyses at 4 and 10 $\mu$m thickness are cut using a Reichert-Jung Polycut S microtome. The 4 $\mu$m sections are stained with modified Masson's Trichrome stain while the 10 $\mu$m sections remained unstained. One 4 $\mu$m and one 10 $\mu$m sections from each rat are used for cancellous bone histomorphometry.

Cross sections of tibial shaft at 10 $\mu$m thickness are cut using a Reichert-Jung Polycut S microtome. These sections are used for cortical bone histomorphometric analysis.

Cancellous bone histomorphometry: A Bioquant OS/2 histomorphometry system (R&M Biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa.

The 4 μm sections are used to determine indices related to bone volume, bone structure, and bone resorption, while the 10 μm sections are used to determine indices related to bone formation and bone turnover.

I) Measurements and calculations related to trabecular bone volume and structure: (1) Total metaphyseal area (TV, mm²): metaphyseal area between 1.2 and 3.6 mm distal to the growth plate-epiphyseal junction. (2) Trabecular bone area (BV, mm²): total area of trabeculae within TV. (3) Trabecular bone perimeter (BS, mm): the length of total perimeter of trabeculae. (4) Trabecular bone volume (BV/TV, %): BV/TV×100. (5) Trabecular bone number (TBN, #/mm): 1.199/2×BS/TV. (6) Trabecular bone thickness (TBT, μm): (2000/1.199)×(BV/BS). (7) Trabecular bone separation (TBS, μm): (2000×1.199)×(TV−BV).

II) Measurements and calculations related to bone resorption: (1) Osteoclast number (OCN, #): total number of osteoclast within total metaphyseal area. (2) Osteoclast perimeter (OCP, mm): length of trabecular perimeter covered by osteoclast. (3) Osteoclast number/mm (OCN/mm, #/mm): OCN/BS. (4) Percent osteoclast perimeter (%OCP, %): OCP/BS×100.

III) Measurements and calculations related to bone formation and turnover: (1) Single-calcein labeled perimeter (SLS, mm): total length of trabecular perimeter labeled with one calcein label. (2) Double-calcein labeled perimeter (DLS, mm): total length of trabecular perimeter labeled with two calcein labels. (3) Inter-labeled width (ILW, μm): average distance between two calcein labels. (4) Percent mineralizing perimeter (PMS, %): (SLS/2+DLS)/BS×100. (5) Mineral apposition rate (MAR, μm/day): ILW/label interval. (6) Bone formation rate/surface ref. (BFR/BS, μm²/d/μm): (SLS/2+DLS)×MAR/BS. (7) Bone turnover rate (BTR, %/y): (SLS/2+DLS)×MAR/BV×100.

Cortical bone histomorphometry: A Bioquant OS/2 histomorphometry system (R&M Biometrics, Inc., Nashville, Tenn.) is used for the static and dynamic histomorphometric measurements of tibial shaft cortical bone. Total tissue area, marrow cavity area, periosteal perimeter, endocortical perimeter, single labeled perimeter, double labeled perimeter, and interlabeled width on both periosteal and endocortical surface are measured, and cortical bone area (total tissue area−marrow cavity area), percent cortical bone area (cortical area/total tissue area×100), percent marrow area (marrow cavity area/total tissue area×100), periosteal and endocortical percent labeled perimeter [(single labeled perimeter/2+double labeled perimeter)/total perimeter× 100], mineral apposition rate (interlabeled width/intervals), and bone formation rate [mineral apposition rate×[(single labeled perimeter/2+double labeled perimeter)/total perimeter] are calculated.

Statistics

Statistics can be calculated using StatView 4.0 packages (Abacus Concepts, Inc., Berkeley, Calif.). The analysis of variance (ANOVA) test followed by Fisher's PLSD (Stat View, Abacus Concepts Inc., 1918 Bonita Ave, Berkeley, Calif. 94704-1014) are used to compare the differences between groups.

Determination of CAMP Elevation in 293-S Cell Lines Stably Overexpressing Recombinant Human $EP_2$ and $EP_4$ Receptors cDNAs representing the complete open reading frames of the human $EP_2$ and $EP_4$ receptors are generated by reverse transcriptase polymerase chain reaction using oligonucleotide primers based on published sequences (1, 2) and RNA from primary human kidney cells ($EP_2$) or primary human lung cells ($EP_4$) as templates. cDNAs are cloned into the multiple cloning site of pcDNA3 (Invitrogen Corporation, 3985B Sorrento Valley Blvd., San Diego, Calif. 92121) and used to transfect 293-S human embryonic kidney cells via calcium phosphate co-precipitation. G418-resistant colonies are expanded and tested for specific [$^3$H]PGE$_2$ binding. Transfectants demonstrating high levels of specific [$^3$H] PGE$_2$ binding are further characterized by Scatchard analysis to determine Bmax and Kds for PGE$_2$. The lines selected for compound screening have approximately 338,400 receptors per cell and a Kd=12 nM for PGE$_2$ (EP$_2$), and approximately 256,400 receptors per cell and a Kd=2.9 nM for PGE$_2$ (EP$_4$). Constituitive expression of both receptors in parental 293-S cells is negligible. Cells are maintained in RPMI supplemented with fetal bovine serum (10% final) and G418 (700 ug/ml final).

cAMP responses in the 293-S/EP$_2$ and 293-S/EP$_4$ lines are determined by detaching cells from culture flasks in 1 ml of Ca++ and Mg++ deficient PBS via vigorous pounding, adding serum-free RPMI to a final concentration of 1×10$^6$ cells/ml, and adding 3-isobutyl-1-methylxanthine (IBMX) to a final concentration of 1 mM. One milliliter of cell suspension is immediately aliquoted into individual 2 ml screwcap microcentrifuge and incubated for 10 minutes, uncovered, at 37° C., 5% CO$_2$, 95% relative humdity. The compound to be tested is then added to cells at 1:100 dilutions such that final DMSO or ethanol concentrations is 1%. Immediately after adding compound, the tubes are covered, mixed by inverting two times, and incubated at 37° C. for 12 minutes. Samples are then lysed by incubation at 100° C. for 10 minutes and immediately cooled on ice for 5 minutes. Cellular debris is pelleted by centrifugation at 1000× g for 5 minutes, and cleared lysates are transferred to fresh tubes. cAMP concentrations are determined using a commercially available cAMP radioimmunoassay kit RIA (NEK-033, DuPont/NEN Research Products, 549 Albany St., Boston, Mass. 02118) after diluting cleared lysates 1:10 in cAMP RIA assay buffer (included in kit). Typically, one treats cells with 6–8 concentrations of the compound to be tested in 1 log increments. EC50 calculations are performed on a calculator using linear regression analysis on the linear portion of the dose response curves.

References

1. Regan, J. W. Bailey, T. J. Pepperl, D. J. Pierce, K. L. Bogardus, A. M. Donello, J. E. Fairbairn, C. E. Kedzie, K. M. Woodward, D. F. and Gil, D. W. 1994 Cloning of a Novel Human Prostaglandin Receptorwith Characteristics of the Pharmaclogically Defined EP$_2$ Subtype. Mol. Pharmacology 46:213–220.
2. Bastien, L., Sawyer, N., Grygorczyk, R., Metters, K., and Adam, M. 1994 Cloning, Functional Expression, and Characterization of the Human Prostaglandin E2 Receptor EP2 Subtype. J. Biol. Chem. Vol 269, 16:11873–11877.

Assay for Binding to Prostaglandin E$_2$ Receptors

Membrane Preparation: All operations are performed at 4° C. Transfected cells expressing prostaglandin E$_2$ type 1 receptors (EP$_1$), type 2 (EP$_2$), type 3 (EP$_3$) or type 4 (EP$_4$) receptors are harvested and suspended to 2 million cells per ml in Buffer A [50 mM Tris-HCl (pH 7.4), 10 mM MgCl$_2$, 1 mM EDTA, 1 mM Pefabloc peptide, (Boehringer Mannheim Corp., Indianapolis, Ind.), 10 uM Phosporamidon peptide, (Sigma, St. Louis, Mo.), 1 uM pepstatin A peptide, (Sigma, St. Louis, Mo.), 10 uM elastatinal peptide, (Sigma, St. Louis, Mo.), 100 uM antipain peptide, (Sigma, St. Louis, Mo.)]. The cells are lysed by sonification with a Branson Sonifier (Model #250, Branson Ultrasonics Corporation, Danbury, Conn.) in 2 fifteen second bursts. Unlysed cells and debris are removed by centrifugation at 100× g for 10 min. Membranes are then harvested by centrifugation at 45,000× g for 30 minutes. Pelleted membranes are resuspended to 3–10 mg protein per ml, protein concentration being determined of the method of Bradford [Bradford, M., Anal. Biochem., 72, 248 (1976)]. Resuspended membranes are then stored frozen at −80° C. until use.

Binding Assay: Frozen membranes prepared as above are thawed and diluted to 1 mg protein per ml in Buffer A above. One volume of membrane preparation is combined with 0.05 volume test compound or buffer and one volume of 3 nM $^3$H-prostaglandin $E_2$ (#TRK 431, Amersham, Arlington Heights, Ill.) in Buffer A. The mixture (205 µL total volume) is incubated for 1 hour at 25° C. The membranes are then recovered by filtration through type GF/C glass fiber filters (#1205-401, Wallac, Gaithersburg, Md.) using a Tomtec harvester (Model Mach II/96, Tomtec, Orange, Conn.). The membranes with bound $^3$H-prostaglandin $E_2$ are trapped by the filter, while the buffer and unbound $^3$H-prostaglandin $E_2$ pass through the filter into waste. Each sample is then washed 3 times with 3 ml of [50 mM Tris-HCl (pH 7.4), 10 mM $MgCl_2$, 1 mM EDTA]. The filters are then dried by heating in a microwave oven. To determine the amount of $^3$H-prostaglandin bound to the membranes, the dried filters are placed into plastic bags with scintillation fluid and counted in a LKB 1205 Betaplate reader (Wallac, Gaithersburg, Md.). IC50s are determined from the concentration of test compound required to displace 50% of the specifically bound $^3$H-prostaglandin $E_2$.

The full length $EP_1$ receptor is made as disclosed in Funk et al., Journal of Biological Chemistry, 1993, 268, 26767–26772. The full length $EP_2$ receptor is made as disclosed in Regan et al., Molecular Pharmacology, 1994, 46, 213–220. The full length $EP_3$ receptor is made as disclosed in Regan et al., British Journal of Pharmacology, 1994, 112, 377–385. The full length $EP_4$ receptor is made as disclosed in Bastien, Journal of Biological Chemistry, 1994, 269,11873–11877. These full length receptors are used to prepare 293S cells expressing the $EP_1$, $EP_2$, $EP_3$ and $EP_4$ receptors.

293S cells expressing either the human $EP_1$, $EP_2$, $EP_3$ or $EP_4$ prostaglandin $E_2$ receptors are generated according to methods known to those skilled in the art. Typically, PCR (polymerase chain reaction) primers corresponding to the 5' and 3' ends of the published full length receptor are made according to the well known methods disclosed above and are used in an RT-PCR reaction using the total RNA from human kidney (for $EP_1$), human lung (for $EP_2$) or human lung (for $EP_3$) as a source. PCR products are cloned by the TA overhang method into pCR2.1 (Invitrogen, Carlsbad, Calif.) and identity of the cloned receptor is confirmed by DNA sequencing.

293S cells (Mayo, Dept. of Biochemistry, Northwestern Univ.) are transfected with the cloned receptor in pcDNA3 by electroporation. Stable cell lines expressing the receptor are established following selection of transfected cells with G418.

Clonal cell lines expressing the maximal number of receptors are chosen following a whole cell $^3$H-$PGE_2$ binding assay using unlabeled $PGE_2$ as a competitor.

Fracture Healing Assays

Assay for Effects on Fracture Healing After Systemic Administration

Fracture Technique: Sprage-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10–12 animals per each subgroup per time point for testing the fracture healing. The first group receives daily gavage of vehicle (water: 100% Ethnanol=95:5) at 1 ml/rat, while the others receive daily gavage from 0.01 to 100 mg/kg/day of the compound to be tested (1 ml/rat) for 10, 20, 40 and 80 days.

At 10, 20, 40 and 80 days, 10–12 rats from each group are anesthetized with Ketamine and sacrificed by exsanguination. Both tibiofibular bones are removed by dissection and all soft tissue is stripped. Bones from 5–6 rats for each group are stored in 70% ethanol for histological analysis, and bones from another 5–6 rats for each group are stored in a buffered Ringers solution (+4° C., pH 7.4) for radiographs and biomechanical testing which is performed.

Histological Analysis: The methods for histologic analysis of fractured bone have been previously published by Mosekilde and Bak (The Effects of Growth Hormone on Fracture Healing in Rats: A Histological Description. Bone, 14:19–27, 1993). Briefly, the fracture side is sawed 8 mm to each side of the fracture line, embedded undecalcified in methymethacrylate, and cut frontals sections on a Reichert-Jung Polycut microtome in 8 µm thick. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Assay for Effects on Fracture Healing After Local Administration

Fracture Technique: Female or male beagle dogs at approximately 2 years of age are used under anesthesia in the study. Transverse radial fractures are produced by slow continuous loading in three-point bending as described by Lenehan et al. (Lenehan, T. M.; Balligand, M.; Nunamaker, D. M.; Wood, F. E.: Effects of EHDP on Fracture Healing in Dogs. J Orthop Res 3:499–507; 1985). A wire is pulled through the fracture site to ensure complete anatomical disruption of the bone. Thereafter, local delivery of prostaglandin agonists to the fracture site is achieved by slow release of compound delivered by slow release pellets or by administration of the compounds in a suitable formulation such as a paste gel solution or suspension for 10, 15, or 20 weeks.

Histological Analysis: The methods for histologic analysis of fractured bone have been previously published by Peter et al. (Peter, C. P.; Cook, W. O.; Nunamaker, D. M.; Provost, M. T.; Seedor, J. G.; Rodan, G. A. Effects of alendronate on fracture healing and bone remodeling in dogs. J. Orthop. Res. 14:74–70, 1996) and Mosekilde and Bak (The Effects of Growth Hormone on Fracture Healing in Rats: A Histological Description. Bone, 14:19–27, 1993). Briefly, after sacrifice, the fracture side is sawed 3 cm to each side of the fracture line, embedded undecalcified in methymethacrylate, and cut on a Reichert-Jung Polycut microtome in 8 $\mu$m thick of frontal sections. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, (6) cartilage area in the callus.

Biomechanical Analysis: The methods for biomechanical analysis have been previously published by Bak and Andreassen (The Effects of Aging on Fracture Healing in Rats. Calcif Tissue Int 45:292–2971 1989) and Peter et al. (Peter, C. P.; Cook, W. O.; Nunamaker, D. M.; Provost, M. T.; Seedor, J. G.; Rodan, G. A. Effects of Alendronate On Fracture Healing And Bone Remodeling In Dogs. J. Orthop. Res. 14:74–70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

Estrogen Agonist/Antagonist Protocol

Estrogen agonist/antagonists are a class of compounds which inhibit bone turnover and prevent estrogen-deficiency induced bone loss. The ovariectomized rat bone loss model has been widely used as a model of postmenopausal bone loss. Using this model, one can test the efficacy of the estrogen agonist/antagonist compounds in preventing bone loss and inhibiting bone resorption.

Sprague-Dawley female rats (Charles River, Wilmington, Mass.) at different ages (such as 5 months of age) are used in these studies. The rats are singly housed in 20 cm×32 cm×20 cm cages during the experimental period. All rats are allowed free access to water and a pelleted commercial diet (Agway ProLab 3000, Agway County Food, Inc., Syracuse, N.Y.) containing 0.97% calcium, 0.85% phosphorus, and 1.05 IU/g of Vitamin $D_3$ A group of rats (8 to 10) are sham-operated and treated p.o. with vehicle (10% ethanol and 90% saline, 1 ml/day), while the remaining rats are bilaterally ovariectomized (OVX) and treated with either vehicle (p.o.), 17$\beta$-estradiol (Sigma, E-8876, $E_2$, 30 $\mu$g/kg, daily subcutaneous injection), or estrogen agonist/antagonists (such as droloxifene at 5, 10, or 20 mg/kg, daily p.o.) for a certain period (such as 4 weeks). All rats are given subcutaneous injections of 10 mg/kg calcein (fluorochrome bone marker) 12 and 2 days before being sacrificed in order to examine the dynamic changes in bone tissue. After 4 weeks of treatment, the rats are sacrificed and autopsied. The following endpoints are determined:

Body Weight Gain: Body weight at autopsy minus body weight at surgery.

Uterine Weight and Histology: The uterus is removed from each rat during autopsy, and weighed immediately. Thereafter, the uterus is processed for histologic measurements such as uterine cross-sectional tissue area, stromal thickness, and luminal epithelial thickness.

Total Serum Cholesterol: Blood is obtained by cardiac puncture and allowed to clot at 4° C., and then centrifuged at 2,000 g for 10 min. Serum samples are analyzed for total serum cholesterol using a high performance cholesterol calorimetric assay (Boehringer Mannheim Biochemicals, Indianapolis, Ind.).

Femoral Bone Mineral Measurements: The right femur from each rat is removed at autopsy and scanned using dual energy X-ray absorptiometry (DEXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) is determined.

Proximal Tibial Metaphyseal Cancellous Bone Histomorphometric Analyses: The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 $\mu$m thickness are cut using a Reichert-Jung Polycut S microtome. One 4 $\mu$m and one 10 $\mu$m sections from each rat are used for cancellous bone histomorphometry. The 4 $\mu$m sections are stained with modified Masson's Trichrome stain while the 10 $\mu$m sections remained unstained.

A Bioquant OS/2 histomorphometry system (R&M Biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region is omitted in order to restrict measurements to the secondary spongiosa. The 4 $\mu$m sections are used to determine indices related to bone volume, bone structure, and bone resorption, while the 10 $\mu$m sections are used to determine indices related to bone formation and bone turnover.

I. Measurements and calculations related to trabecular bone volume and structure:

1. Total metaphyseal area (TV, $mm^2$): metaphyseal area between 1.2 and 3.6 mm distal to the growth plate-epiphyseal junction.

2. Trabecular bone area (BV, mm$^2$): total area of trabeculae within TV.

3. Trabecular bone perimeter (BS, mm): the length of total perimeter of trabeculae.

4. Trabecular bone volume (BV/TV, %): BV/TV×100.

5. Trabecular bone number (TBN, #/mm): 1.199/2×BS/TV.

6. Trabecular bone thickness (TBT, μm): (2000/1.199)×(BV/BS).

7. Trabecular bone separation (TBS, μm): (2000×1.199)×(TV−BV).

II. Measurements and calculations related to bone resorption:

1. Osteoclast number (OCN, #): total number of osteoclast within total metaphyseal area.

2. Osteoclast perimeter (OCP, mm): length of trabecular perimeter covered by osteoclast.

3. Osteoclast number/mm (OCN/mm, #/mm): OCN/BS.

4. Percent osteoclast perimeter (%OCP, %): OCP/BS×100.

III. Measurements and calculations related to bone formation and turnover:

1. Single-calcein labeled perimeter (SLS, mm): total length of trabecular perimeter labeled with one calcein label.

2. Double-calcein labeled perimeter (DLS, mm): total length of trabecular perimeter labeled with two calcein labels.

3. Inter-labeled width (ILW, μm): average distance between two calcein labels.

4. Percent mineralizing perimeter (PMS, %): (SLS/2+DLS)/BS×100.

5. Mineral apposition rate (MAR, μm/day): ILW/label interval.

6. Bone formation rate/surface ref. (BFR/BS, μm$^2$/d/μm): (SLS/2+DLS)×MAR/BS.

7. Bone turnover rate (BTR, %/y): (SLS/2+DLS)×MAR/BV×100.

Statistics

Statistics are calculated using StatView 4.0 packages (Abacus Concepts, Inc., Berkeley, Calif.). The analysis of variance (ANOVA) test followed by Fisher's PLSD (Stat View, Abacus Concepts Inc. 1918 Bonita Ave, Berkeley, Calif. 94704-1014) is used to compare the differences between groups.

Combination and Sequential Treatment Protocol

The following protocols can of course be varied by those skilled in the art. For example, intact male or female rats, sex hormone deficient male (orchidectomy) or female (ovariectomy) rats may be used. In addition, male or female rats at different ages (such as 12 months of age) can be used in the studies. The rats can be either intact or castrated (ovariectomized or orchidectomized), and administered with anabolic agents such as the compounds of this invention at different doses (such as 1, 3 or 6 mg/kg/day) for a certain period (such as two weeks to two months), and followed by administration of an anti-resorptive agent such as droloxifene at different doses (such as 1,5,10 mg/kg/day) for a certain period (such as two weeks to two months), or a combination treatment with both anabolic agent and anti-resorptive agent at different doses for a certain period (such as two weeks to two months). In the castrated rats, treatment can be started on the next day after surgery (for the purpose of preventing bone loss) or at the time bone loss has already occurred (for the purpose of restoring bone mass).

The rats are sacrificed under ketamine anesthesia. The following endpoints are determined:

Femoral bone mineral measurements are performed as described above in the estrogen agonist/antagonist protocol.

Lumbar Vertebral Bone Mineral Measurements: Dual energy X-ray absorptiometry (QDR 1000/W, Hologic, Inc., Waltham, Mass.) equipped with a "Regional High Resolution Scan" software (Hologic, Inc., Waltham, Mass.) is used to determined the bone area, bone mineral content (BMC), and bone mineral density (BMD) of whole lumbar spine and each of the six lumbar vertebrae (LV1-6) in the anesthetized rats. The rats are anesthetized by injection (i.p.) of 1 ml/kg of a mixture of ketamine/rompun (ratio of 4 to 3), and then placed on a rat platform. The scan field sized is 6×1.9 cm, resolution is 0.0254×0.0127 cm, and scan speed is 7.25 mm/sec. The whole lumbar spine scan image is obtained and analyzed. Bone area (BA), and bone mineral content (BMC) is determined, and bone mineral density is calculated (MBC divided by BA) for the whole lumbar spine and each of the six lumbar vertebrae (LV1-6).

Proximal tibial metaphyseal cancellous bone histomorphometric analyses are performed as described above for in the estrogen agonistlantagonist protocol.

Measurements and calculations related to trabecular bone volume and structure are performed as described above in the estrogen agonist/antagonist protocol. Further, measurements and calculations related to bone resorption are also performed as described above in the estrogen agonist/antagonist protocol. Still further, measurements and calculations related to bone formation and turnover are performed as described above in the estrogen agonist/antagonist protocol. Further still, the data obtained is analyzed using the statistical manipulations described above in the estrogen agonist/antagonist protocol.

Kidney Regeneration Assay

The role of an prostaglandin selective agonist in kidney regeneration is investigated by the ability of Prostaglandin $E_2$ (PGE$_2$) or a selective prostaglandin agonist to induce the expression of Bone Morphogenetic Protein 7 (BMP-7) in wild type 293S cells and in 293S cells transfected with EP$_2$.

Methods: 293S and EP$_2$ 293S cells are grown in Dulbecco's Modified Egale medium (DMEM, Gibco, BRL; Gaithersburg, Md.). One day prior to treatment with PGE$_2$ or an prostaglandin agonist, cells are plated at a density of 1.5×10$^6$ cells/10 cm dish. Generally about 16 to 24 hours later the cell monolayer is washed once with OptiMEM (Gico, BRL) followed by the addition of 10 ml OptiMEM/dish in the presence and absense of vehicle (DMSO), PGE$_2$ (10$^{-6}$M) or an prostaglandin selective agonist (10$^{-6}$M). Cells are harvested and RNA is extracted at 8, 16 and 24 hours. Northern blot analysis of total (20 mg/lane) is carried out by probing the blots with $^{32}$P-labeled BMP-7 probe. The blots are normalized for RNA loading by hybridization with $^{32}$P-labeled 18s ribosomal RNA probe. PGE$_2$ and prostaglandin selective agonists induce the expression of BMP-7 in the EP$_2$ 293S cells in a time dependent manner. Such induction of expression is generally not observed in the parental cell line. Given the known role of BMP-7 in kidney regeneration and the ability of an prostaglandin agonist to induce BMP-7 expression in 293S kidney cells in a time and receptor specific manner indicates a role for prostaglandin agonist in kidney regeneration.

Administration of the compounds of this invention can be via any method which delivers a compound of this invention systemically and/or locally (e.g., at the site of the bone fracture, osteotomy, or orthopedic surgery). These methods include oral routes, parenteral, intraduodenal routes, etc.

Generally, the compounds of this invention are administered orally, but parenteral administration (e.g., intravenous, intramuscular, transdermal, subcutaneous, rectal or intramedullary) may be utilized, for example, where oral administration is inappropriate for the target or where the patient is unable to ingest the drug.

The compounds are used for the treatment and promotion of healing of bone fractures and osteotomies by the local application (e.g., to the sites of bone fractures of osteotomies) of the compounds of this invention or compositions thereof. The compounds of this invention are applied to the sites of bone fractures or osteotomies, for example, either by injection of the compound in a suitable solvent (e.g., an oily solvent such as arachis oil) to the cartilage growth plate or, in cases of open surgery, by local application thereto of such compounds in a suitable carrier or diluent such as bone-wax, demineralized bone powder, polymeric bone cements, bone sealants, etc. Alternatively, local application can be achieved by applying a solution or dispersion of the compound in a suitable carrier or diluent onto the surface of, or incorporating it into solid or semisolid implants conventionally used in orthopedic surgery, such as dacron-mesh, gel-foam and kiel bone, or prostheses.

The compounds of this invention may also be applied locally to the site of the fracture or osteotomy in a suitable carrier or diluent in combination with one or more of the anabolic agents or bone anti-resorptive agents described above.

Such combinations within the scope of this invention can be co-administered simultaneously or sequentially in any order, or a single pharmaceutical composition comprising a Formula I compound, a prodrug thereof or a pharmaceutical salt of said compound or said prodrug as described above and a second compound as described above in a pharmaceutically acceptable carrier or diluent can be administered.

For example, a bone anabolic agent can be used in this invention alone or in combination with an anti-resorptive agent for three months to three years, followed by an anti-resorptive agent alone for three months to three years, with optional repeat of the full treatment cycle. Alternatively, for example, the bone anabolic agent can be used alone or in combination with an anti-resorptive agent for three months to three years, followed by an anti-resorptive agent alone for the remainder of the patient's life. For example, in one preferred mode of administration, a Formula I, II or III compound, or a prodrug thereof or a pharmaceutically acceptable salt of said compound or said prodrug as described above may be administered once daily and a second compound as described above (e.g., estrogen agonist/antagonist) may be administered daily in single or multiple doses. Alternatively, for example, in another preferred mode of administration the two compounds may be administered sequentially wherein the Formula I, II or III compound, prodrug thereof or pharmaceutically acceptable salt of said compound or said prodrug as described above may be administered once daily for a period of time sufficient to augment bone mass to a level which is above the bone fracture threshold (World Health Organization Study "Assessment of Fracture Risk and its Application to Screening for Postmenopausal Osteoporosis (1994). Report of a World Health Organization Study Group. World Health Organization Technical Series 843") followed by administration of a second compound, as described above (e.g., estrogen agonist/antagonist), daily in single or multiple doses. It is preferred that the first compound as described above is administered once daily in a rapid delivery form such as oral delivery.

In any event, the amount and timing of compounds administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the treatment (e.g. bone mass augmentation) that the physician considers appropriate for the patient. In considering the degree of treatment desired, the physician must balance a variety of factors such as bone mass starting level, age of the patient, presence of preexisting disease, as well as presence of other diseases (e.g., cardiovascular disease).

In general an amount of a compound of this invention is used that is sufficient to augment bone mass to a level which is above the bone fracture threshold (as detailed in the World Health Organization Study previously cited herein).

In general an effective dosage for the anabolic agents used in this invention described above is in the range of 0.001 to 100 mg/kg/day, preferably 0.01 to 50 mg/kg/day.

The following paragraphs provide preferred dosage ranges for various anti-resorptive agents.

The amount of the anti-resorptive agent to be used is determined by its activity as a bone loss inhibiting agent. This activity is determined by means of the pharmacokinetics of an individual compound and its minimal versus maximal effective dose in inhibition of bone loss using a protocol such as described above (e.g., Estrogen Agonist/Antagonist Protocol).

In general, an effective dosage for an anti-resorptive agent is about 0.001 mg/kg/day to about 20 mg/kg/day.

In general, an effective dosage for progestins is about 0.1 to 10 mg per day; the preferred dose is about 0.25 to 5 mg per day.

In general, an effective dosage for polyphosphonates is determined by its potency as a bone resorption inhibiting agent according to standard assays.

Ranges for the daily administration of some polyphosphonates are about 0.001 mg/kg/day to about 20 mg/kg/day.

In general an effective dosage for the treatment of this invention, for example the bone resorption treatment of this invention, for the estrogen agonists/antagonists of this invention is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for 2-(4-methoxy-phenyl)-3-[4-(2-piperidin-1-yl-ethoxy)-phenoxy]-benzo[b]thiophen-6-ol is 0.001 to 1 mg/kg/day.

In particular, an effective dosage for cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8tetrahydro-naphthalene-2-ol; or 1-(4'-pyrrolidinolethoxyphenyl)-2-phenyl-6-hydroxy-1,2,3,4-tetrahydroisoquinoline is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

The compounds of the present invention are generally administered in the form of a pharmaceutical composition comprising at least one of the compounds of this invention together with a pharmaceutically acceptable vehicle or diluent. Thus, the compounds of this invention can be administered individually or together, locally or systemically, in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) of this invention in an amount effective to treat the disease/condition of the subject being treated, e.g., a bone disorder.

Since the present invention has an aspect that relates to the augmentation and maintenance of bone mass by treatment with a combination of active ingredients which may be administered separately, the invention also relates to combining separate pharmaceutical compositions in kit form. The kit comprises two separate pharmaceutical compositions: a compound of Formula I, II or III, a prodrug thereof or a pharmaceutically acceptable salt of said compound or said prodrug and a second compound as described above. The kit comprises container means for containing the separate compositions such as a divided bottle or a divided foil packet, however, the separate compositions may also be contained within a single, undivided container. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the dosage form so specified should be ingested. Another example of such a memory aid is a calendar printed on the card e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day. Also, a daily dose of a Formula I, II or III compound, a prodrug thereof or a pharmaceutically acceptable salt of said compound or said prodrug can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention either alone or in combination with each other or other compounds generally will be administered in a convenient formulation. The following formulation examples only are illustrative and are not intended to limit the scope of the present invention.

In the formulations which follow, "active ingredient" means a compound or compounds of this invention.

Formulation 1: Gelatin Capsules

Hard gelatin capsules are prepared using the following:

| Ingredient | Quantity (mg/capsule) |
| --- | --- |
| Active ingredient | 0.25–100 |
| Starch NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicone dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidine (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 20 mg |
| Isotonic saline | 1,000 mL |

The solution of the above ingredients is intravenously administered to a patient at a rate of about 1 mL per minute.

The active ingredient above may also be a combination of agents.

The abbreviations "Me", "Et", "tPr", "Tf", "Bu", "Ph", "EDC" and "Ac", where used herein, define the terms "methyl," "ethyl", "isopropyl", "triflyl", "butyl", "phenyl", "1-(3-dimethylaminopropyl)-3-ethyl-carbodiimide hydrochloride" and "acetyl", respectively.

General Experimental Procedures

Unless otherwise specified, all reactions were performed under an inert atmosphere such as nitrogen ($N_2$).

NMR spectra were recorded on a Varian XL-300 (Varian Co., Palo Alto, Calif.), a Bruker AM-300 spectrometer (Bruker Co., Billerica, Mass.) or a Varian Unity 400 at about 23° C. at 300 or 400 MHz for proton and 75.4 MHz for carbon nuclei. Chemical shifts are expressed in parts per million downfield from trimethylsilane. The peak shapes are denoted as follows: s, singlet; d, doublet; t, triplet, q, quartet; m, multiplet; bs=broad singlet. Resonances designated as exchangeable did not appear in a separate NMR experiment where the sample was shaken with several drops of $D_2O$ in the same solvent. Atmospheric pressure chemical ionization (APCI) mass spectra were obtained on a Fisons Platform II Spectrometer. Chemical ionization mass spectra were obtained on a Hewlett-Packard 5989 instrument (Hewlett-Packard Co., Palo Alto, Calif.) (ammonia ionization, PBMS). Where the intensity of chlorine or bromine-containing ions are described the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

Column chromatography was performed with either Baker Silica Gel (40 μm) (J. T. Baker, Phillipsburg, N.J.) or Silica Gel 60 (EM Sciences, Gibbstown, N.J.) in glass columns under low nitrogen pressure. Radial Chromatography was performed using a Chromatotron® (model 7924T, Harrison Research). Medium pressure chromatography was performed on a Flash 40 Biotage System (Biotage Inc, Dyax Corp., Charlottesville, Va.). Unless otherwise specified, reagents were used as obtained from commercial sources. Dimethylformamide, 2-propanol, acetonitrile, methanol, tetrahydrofuran, and dichloromethane, when used as reaction solvents, were the anhydrous grade supplied by Aldrich Chemical Company (Milwaukee, Wis.). The terms "concentrated" and "coevaporated" refer to removal of solvent at water aspirator pressure on a rotary evaporator with a bath temperature of less than 45° C. Reactions conducted at "0–20° C." or "0–25° C." were conducted with initial cooling of the vessel in an insulated ice bath which was allowed to warm to room temperature over several hours. The abbreviation "min" and "h" stand for "minutes" and "hours" respectively.

EXAMPLE 1

7-((4-Hydroxy-nonyl)-methanesulfonyl-amino)-heptanoic acid

The title compound was prepared as described in U.S. Pat. No. 4,033,996. $^1H$ NMR ($CDCl_3$) δ 3.62–3.60 (m, 1H), 3.19–3.10 (m, 4H), 2.80 (s, 3H), 2.33 (m, 2H), 1.81–1.69 (m, 1H), 1.67–1.55 (m, 5H), 1.52–1.26 (m, 15H), 0.87 (t, 3H); MS 364 ($M^+$–1).

EXAMPLE 2

8-Acetyl-12-hydroxy-heptadecanoic acid

The title compound was prepared as described in U.S. Pat. No. 4,018,802. $^1H$ NMR ($CDCl_3$) δ 3.60–3.52 (m, 1H), 2.43–2.38 (m, 1H), 2.34–2.30 (m, 2H), 2.10 (s, 3H), 1.62–1.53 (m, 4H), 1.40–1.23 (m, 22H), 0.87 (t, 3H); MS 327 ($M^+$–1).

EXAMPLE 3

(3-(((4-Hydroxy-nonyl)-methanesulfonyl-amino)-methyl)-phenoxy)-acetic acid

The title compound was prepared from [3-(methanesulfonylamino-methyl)phenoxy]-acetic acid methyl ester (Preparation 10) and acetic acid 1-(3-chloropropyl)-hexyl ester using the alkylation procedure described in U.S. Pat. No. 4,033,996. $^1H$ NMR ($CDCl_3$) δ 7.31–7.26 (m, 1 H), 7.02–6.84 (m, 3H), 4.68 (s, 2H), 4.35 (s, 2H), 3.91–3.89 (m, 1 H), 3.20–3.12 (m, 2H), 2.83 (s, 3H), 1.94–1.92 (m, 1H), 1.79–1.24 (m, 12H), 0.87 (t, 3H); MS 400 ($M^+$–1).

PREPARATION 1

Pyridine-3-sulfonyl chloride hydrochloride

A mixture of pyridine-3-sulfonic acid (15.0 g), phosphorous pentachloride (24.0 g) and phosphorous oxychloride (30 mL) was heated to 120° C. for 16 h. The reaction was cooled to room temperature, and the resulting suspension was saturated with HCl (g). A white precipitate was collected, washed with $CHCl_3$, and dried in vacuo to afford the title compound (15.6 g). $^1H$ NMR (400 MHz, DMSO) δ 8.98 (s, 1H), 8.85 (d, 1H), 8.66 (d, 1H), 8.02 (t, 1H).

PREPARATION 2

5-(3-Amino-propyl)-thiophene-2-carboxylic acid methyl ester

Step A 5-(3-tert-Butoxycarbonylamino-prop-1-ynyl)-thiophene-2-carboxylic acid methyl ester. A mixture of prop-2-ynyl-carbamic acid tert-butyl ester (1.67 g, 0.011 mmol), 5-bromo-thiophene-2-carboxylic acid methyl ester (2.50 g, 0.011 mmol), tetrakistriphenylphosphine(0) palladium (0.622 g, 0.0538 mmol), CuI (0.102 g, 0.538 mmol) and triethylamine (1.57 mL, 0.011 mmol) in 50 mL acetonitrile was heated at reflux for 16 h. The reaction was cooled to room temperature, diluted with 75 mL EtOAc, washed with 5.5% HCl, water and brine, dried over $MgSO_4$, filtered and concentrated in vacuo to an oil. The product was purified via flash chromatography (9:1 to 4:1 hexanes:EtOAc) to afford the title compound as an oil (2.06 g). MS 313 (M+18).

Step B 5-(3-tert-Butoxycarbonylamino-propyl)-thiophene-2-carboxylic acid methyl ester. A solution of 5-(3-tert-butoxycarbonylamino-prop-1-ynyl)-thiophene-2-carboxylic acid methyl ester (2.06 g) and 10% Pd/C (1.03 g) in 50 mL MeOH was placed in a Parr shaker and was hydrogenated at 50 psi $H_2$ for 16 h. The reaction was filtered through Celite® with the aid of MeOH and the filtrate was concentrated in vacuo to afford the title compound of Step B as a solid (1.93 g). MS 317 (M+18).

Step C 5-(3-Amino-propyl)-thiophene-2-carboxylic acid methyl ester. A solution of 5-(3-tert-butoxycarbonylamino-propyl)-thiophene-2-carboxylic acid methyl ester (0.118 g, 0.5 mmol) in 50 mL MeOH was cooled to 0° C. and was saturated with HCl (g). The reaction was stirred at room temperature for 90 minutes. The solution was concentrated to a solid which was partitioned between EtOAc and saturated $NaHCO_3$. The layers were separated, and the organic solution was washed with brine, dried over $MgSO_4$, filtered and concentrated in vacuo to afford the title compound as an oil (399 mg). MS 200 (M+1).

PREPARATION 2a 5-(3-Amino-propyl)-furan-2-carboxylic acid methyl ester hydrochloride salt Preparation 2a was prepared from the appropriate starting materials in an analogous manner to Preparation 2 with the following exceptions. The hydrogenation performed in Step B was carried out for 5.5 h. In Step C, the reaction was stirred for 16 h at room temperature and was concentrated in vacuo to provide the title compound as the hydrochloride salt.

PREPARATION 3

5-(3-Methanesulfonylamino-propyl)-furan-2-carboxylic acid methyl ester

To a solution of 5-(3-amino-propyl)-furan-2-carboxylic acid methyl ester hydrochloride salt (see Preparation 2a) (150 mg, 0.683 mmol), and triethylamine (0.313 mL, 2.25 mmol) in $CH_2Cl_2$ (15 mL) at 0° C. was added methanesulfonyl chloride (86 mg, 0.75 mmol). The reaction was stirred at room temperature for 18 h. The organic solution was washed consecutively with dilute HCl, water, saturated $NaHCO_3$, and brine. The organic solution was dried over $MgSO_4$, filtered, and concentrated to provide the title sulfonamide (156 mg). MS 262 (M+1).

PREPARATION 4

5-(3-Amino-Propyl)-thiophene-2-carboxylic acid tert-butyl ester

Step A

Prop-2-ynyl-carbamic acid benzyl ester. To a solution of propargylamine (6.4 g, 71.2 mmol) in pyridine (100 mL) was added benzylchloroformate (13.37 g, 78.2 mmol) in 100 mL $CH_2Cl_2$ over 0.5 h. The reaction was stirred for 16 h and the volatiles were removed in vacuo. The residue was dissolved in EtOAc and the organic solution was washed with water (2×). The organic solution was washed with dilute aqueous HCl followed by saturated $NaHCO_3$. The organic solution was dried over $MgSO_4$, filtered, and concentrated in vacuo to provide the title compound of Step A (4.43 g).

Step B 5-(3-Benzyloxycarbonylamino-prop-1-ynyl)-thiophene-2-carboxylic acid tert-butyl ester. The title compound of Step B was prepared from prop-2-ynyl-carbamic acid benzyl ester and 5-bromo-thiophene-2-carboxylic acid tert-butyl ester in an analagous manner to Step A of Preparation 2.

Step C 5-(3-Amino-propyl)-thiophene-2-carboxylic acid tert-butyl ester. To a solution of 5-(3-benzyloxycarbonylamino-prop-1-ynyl)-thiophene-2-carboxylic acid tert-butyl ester (1.0 g, 2.69 mmol) in 15 mL MeOH and 2.69 mL 1N HCl (aq) was added $Pd(OH)_2$. The mixture was placed on a Parr shaker and was hydrogenated under 45 psi $H_2$ for 16 h. The mixture was filtered through Celite®, the catalyst was replaced, and the reaction was shaken for another 6 h. The mixture was filtered through Celite® and concentrated in vacuo. The residue was chased with $CCl_4$ and was triturated with $Et_2O$. The product was isolated as a solid (360 mg).

PREPARATION 5

5-(3-Amino-propyl)-tetrahydrofuran-2-carboxylic acid methyl ester hydrochloride salt Step A 5-(3-tert-Butoxycarbonylamino-prop-1-ynyl)-furan-2-carboxylic acid methyl ester. The title compound of Step A was prepared from 5-bromo-furan-2-carboxylic acid methyl ester and prop-2-ynyl-carbamic acid tert-butyl ester as described in Step A of Preparation 2.

Step B 5-(3-tert-Butoxycarbonylamino-propyl)-tetrahydrofuran-2-carboxylic acid methyl ester and 5-(3-tert-Butoxycarbonylamino-propyl)-furan-2-carboxylic acid methyl ester. To a solution of 5-(3-tert-butoxycarbonylamino-prop-1-ynyl)-furan-2-carboxylic acid methyl ester (1.69 g) in MeOH (50 mL) was added 10% palladium on carbon (850 mg) and the mixture was hydrogenated on a Parr shaker at 50 psi for 18 h. The catalyst was removed via filtration through Celite® and the volatiles were concentrated in vacuo. Flash chromatography (hexanes:EtOAc 4:1) provided 5-(3-tert-butoxycarbonylamino-propyl)-furan-2-carboxylic acid methyl ester (422 mg, MS 284 M+) followed by 5-(3-tert-butoxycarbonylamino-propyl)-tetrahydrofuran-2-carboxylic acid methyl ester (903 mg).

Step C 5-(3-Amino-propyl)-tetrahydrofuran-2-carboxylic acid methyl ester hydrochloride salt. The title compound was prepared from 5-(3-tert-butoxycarbonylaminopropyl)-tetrahydrofuran-2-carboxylic acid methyl ester following the procedure described in Step C for Preparation 2a.

PREPARATION 6

5-(3-Methanesulfonylamino-propyl)-thiophene-2-carboxylic acid methyl ester

Step A 5-(3-Methanesulfonylamino-prop-1-ynyl)-thiophene-2-carboxylic acid methyl ester. To a solution of 5-bromo-thiophene-2-carboxylic acid methyl ester (1.66 g, 8.0 mmol), N-prop-2-ynyl-methanesulfonamide (1.09 g, 8.2 mmol), $Et_3N$ (1.7 mL, 12.1 mmol), and $CH_3CN$ (30 mL) was added $Pd(PPh_3)_4$ (462 mg, 0.4 mmol) followed by CuI (76 mg, 0.4 mmol). The reaction was heated at reflux for 24 h and was cooled to room temperature. The volatiles were removed in vacuo and the residue was purified via flash chromatography (20% EtOAc in hexanes to 33% EtOAc in hexanes) to yield 5-(3-methanesulfonylamino-prop-1-ynyl)-thiophene-2-carboxylic acid methyl ester as a pale yellow solid (1.1 g). $^1$H NMR (300 MHz, $CDCl_3$) δ 7.64 (d, 1H), 7.14 (d, 1H), 4.60 (m, 1H), 4.22 (d, 2H), 3.88 (s, 3H), 3.10 (s, 3H); MS 274 (M+1).

Step B: Hydrogenation

A solution of 5-(3-methanesulfonylamino-prop-1-ynyl)-thiophene-2-carboxylic acid methyl ester (3.0 g, 10.9 mmol) in EtOAc (100 mL) and MeOH (50 mL) was hydrogenated with 10% palladium on carbon (680 mg) at 50 psi for 7 h. The solution was filtered through a pad of Celite® with the aid of MeOH and was concentrated in vacuo to provide the title compound as an off-white solid (2.95 g). $^1$H NMR (300 MHz, $CDCl_3$) δ 7.62 (d, 1H), 7.23 (d, 1H), 4.29 (m, 1H), 3.85 (s, 3H), 3.18 (q, 2H), 2.93 (m, 5H), 1.96 (m, 2H).

PREPARATION 7

(3-Aminomethyl-phenyl)-acetic acid methyl ester hydrochloride

Step A (3-Cyano-phenyl)-acetic acid methyl ester. Nitrogen was bubbled through a mixture of (3-bromo-phenyl)-acetic acid methyl ester (26.12 g, 114.02 mmol), Zn(CN)$_2$ (8.37 g, 71.3 mmol), and DMF (300 mL) for about 5 minutes followed by addition of tetrakistriphenylphosphine(0) palladium (5.0 g, 4.3 mmol). The mixture was heated for 1.5 h at 90° C. and was cooled to room temperature. Aqueous 2N NH$_4$OH was added and the product was extracted into EtOAc (3×). The organic solution was washed with 2N NH$_4$OH (1×) followed by brine (2×). The organic solution was dried (MgSO$_4$), filtered, and concentrated in vacuo. Purification by medium pressure chromatography (9:1 hexanes:EtOAc) provided the title compound of Step A as an oil (18.06 g). $^1$H NMR (400 MHz, CDCl$_3$) δ 7.57–7.41 (m, 4H), 3.706 (s, 3H), 3.703 (s, 2H).

Step B (3-Aminomethyl-phenyl)-acetic acid methyl ester hydrochloride. To a solution of (3-cyano-phenyl)-acetic acid methyl ester (18.06 g, 103 mmol) in MeOH (150 mL) and 4M HCl in dioxane (30.0 mL, 120 mmol) was added 10% palladium on carbon (2 g). The mixture was placed on a Parr shaker and was hydrogenated at 50 psi hydrogen for 24 h. The catalyst was removed via filtration through Celite® and the organic solution was concentrated in vacuo. The resulting solid was stirred in EtOAc and filtered to provide the title compound as a white solid (20.42 g). $^1$H NMR (400 MHz, CD$_3$OD) δ 7.42–7.32 (m, 4H), 4.09 (s, 2H), 3.69 (s, 2H), 3.67 (s, 3H); MS 180 (M+1). mg).

PREPARATION 8

{3-[(Pyridine-3-sulfonylamino)-methyl]-phenyl}-acetic acid methyl ester

To a solution of (3-aminomethyl-phenyl)-acetic acid methyl ester hydrochloride (0.56 g) and diisopropylamine (2.2 mL) in 10 mL dichloromethane was added pyridine-3-sulfonyl chloride (0.601 g, 2.83 mmol) and the reaction was stirred at room temperature for 16 h. Aqueous 1N HCl was added and the solution was extracted with CH$_2$Cl$_2$. The organic solution was washed with saturated NaHCO$_3$, dried over MgSO$_4$, filtered and concentrated in vacuo to afford the title compound. Purification via flash chromatography on silica gel (2:1 hexanes: EtOAc) afforded the title compound as a white solid. $^1$H NMR (400 MHz, CDCl$_3$) δ 8.91 (s, 1H), 8.71 (d, 1H), 8.04 (d, 1H), 7.37 (m, 1H), 7.05–7.24 (m, 4H), 5.87 (bs, 1H), 4.14 (s, 2H), 3.62 (s, 3H), 3.52 (s, 2H).

PREPARATION 9

{3-[(Propane-1-sulfonylamino)-methyl]-phenyl}-acetic acid methyl ester

Following the procedure described in Preparation 8, (3-aminomethyl-phenyl)-acetic acid methyl ester hydrochloride (603 mg, 2.80 mmol) was converted to the title sulfonamide by reaction with 1-propanesulfonyl chloride (0.375 mL) and N,N-diisopropylethylamine (2.0 mL) in dichloroethane (10 mL). $^1$H NMR (400 MHz, CDCl$_3$) δ 7.35–7.22 (m, 4H), 4.60 (bs, 1H), 4.29 (s, 2H), 3.70 (s, 3H), 3.63 (s, 2H), 2.92 (t, 2H), 1.79 (m, 2H), 0.99 (t, 3H).

PREPARATION 10

[3-(Methanesulfonylamino-methyl)-phenoxy]-acetic acid methyl ester

Step A

N-(3-Methoxy-benzyl)-methanesulfonamide. Methanesulfonyl chloride (4.170 g, 36.4 mmol) was added to a solution of 3-methoxybenzylamine (5.000 g, 36.4 mmol) and triethylamine (3.946 g, 39.0 mmol) in THF (100 mL) at room temperature. The mixture was stirred for 18 h and the insolubles were removed by filtration. The organic solution was concentrated to a yellow oil which was purified by flash chromatography (6:4 hexanes:EtOAc to 1:1 hexanes:EtOAc) to yield N-(3-methoxy-benzyl)-methanesulfonamide (7.431 g). $^1$H NMR (400 MHz, CDCl$_3$) δ 7.26 (m, 1H), 6.92–6.82 (m, 3H), 4.62 (m, 1H), 4.28 (d, 2H), 3.80 (s, 3H), 2.87 (s, 3H); MS 214 (M−1).

Step B

N-(3-Hydroxy-benzyl)-methanesulfonamide. A solution of BBr$_3$ (1.0 M in CH$_2$Cl$_2$, 111 mL, 111 mmol) was slowly added to a solution of N-(3-methoxy-benzyl)-methanesulfonamide (12.000 g, 55.7 mmol) in CH$_2$Cl$_2$ (200 mL) 0° C. The reaction was warmed to room temperature and was stirred for 4 h. Methanol (100 mL) was cautiously added and the solution was concentrated in vacuo. Flash chromatography (1:1 hexanes:EtOAc) provided N-(3-hydroxy-benzyl)-methanesulfonamide (11.50 g). $^1$H NMR (400 MHz, CDCl$_3$) δ 7.20 (m, 1H), 6.84 (m, 2H), 6.77 (m, 1H), 4.83 (bs, 1H), 4.24 (s, 2H), 2.86 (s, 3H); MS 201 (M+).

Step C

A mixture of N-(3-hydroxy-benzyl)-methanesulfonamide (6.000 g, 29.82 mmol), methyl bromoacetate (4.562 g, 29.82 mmol), K$_2$CO$_3$ (4.121 g, 29.82 mmol), and acetone (250 mL) was stirred at room temperature for 68 h. The solids were removed by filtration and the solution was concentrated in vacuo. Purification by flash chromatography (1:1 hexanes:EtOAc) provided the title compound of Preparation 10 (5.637 g). $^1$H NMR (400 MHz, CDCl$_3$) δ 7.25 (m, 1H), 6.96 (m, 1H), 6.89 (s, 1H), 6.82 (m, 1H), 4.63 (m, 3H), 4.28 (m, 2H), 3.80 (s, 3H), 2.86 (s, 3H); MS 274 (M+1).

PREPARATION 11

2-(3-Methanesulfonylamino-propyl)-thiazole-4-carboxylic acid ethyl ester

Step A

4-Methanesulfonylamino-butyric acid ethyl ester. Methanesulfonyl chloride (4.10 g, 35.8 mmol) was added to a suspension of ethyl 4-aminobutyrate hydrochloride (6.00 g, 35.8 mmol) and Et$_3$N (10.8 mL, 77.4 mmol) in THF (230 mL). The resulting suspension was stirred at room temperature for 43 h. The reaction mixture was filtered and the filtrate was concentrated. Flash chromatography (1:1 EtOAc:hexanes to EtOAc) afforded the title compound of Step A (7.08 g). $^1$H NMR (400 MHz, CDCl$_3$) δ 4.51 (s, 1H), 4.12 (q, 2H), 3.18 (q, 2H), 2.94 (s, 3H), 2.40 (t, 2H), 1.85–1.92 (m, 2H), 1.24 (t, 3H); MS 210 (M$^+$+1).

Step B

4-Methanesulfonylamino-butyramide. A solution of 4-methanesulfonylamino-butyric acid ethyl ester (7.08 g, 33.8 mmol) in concentrated NH$_4$OH (200 mL) was stirred at room temperature for 66 h. The reaction mixture was concentrated to afford the title compound of Step B as a white solid (6.16 g). The product was used in the next step without further purification. $^1$H NMR (400 MHz, CDCl$_3$) δ 3.30 (s, 3H), 3.05–3.09 (m, 2H), 2.91 (s, 3H), 2.24–2.30 (m, 2H), 1.80–1.85 (m, 2H); MS 181 (M$^+$+1).

Step C

4-Methanesulfonylamino-thiobutyramide. A suspension of 4-methanesulfonylamino-butyramide (0.50 g, 2.8 mmol)

and Lawesson's reagent (0.56 g, 1.4 mmol) in THF (50 mL) was stirred at room temperature for 45 minutes. During this time all of the solid dissolved. The solution was concentrated and purified by flash chromatography (79:1 EtOAc:MeOH) to afford the title compound of Step C (0.41 g); $^1$H NMR (400 MHz, CDCl$_3$) δ 3.29 (s, 3H), 3.07–3.11 (m, 2H), 2.91 (s, 3H), 2.62–2.66 (m, 2H), 1.93–1.99 (m, 2H); MS 197 (M$^+$+1).

Step D 2-(3-Methanesulfonylamino-propyl)-thiazole-4-carboxylic acid ethyl ester. A solution of 4-methanesulfonylamino-thiobutyramide (0.35 g, 1.8 mmol) and ethyl bromopyruvate (0.37 g, 1.9 mmol) in EtOH (50 mL) was stirred at room temperature for 17 h. Additional ethyl bromopyruvate (0.05 g, 0.26 mmol) was added and the reaction mixture was stirred at room temperature for 5.5 h. The reaction mixture was concentrated and was purified by flash chromatography (79:1 to 19:1 EtOAc:MeOH) to afford the title compound (0.47 g). $^1$H NMR (400 MHz, CDCl$_3$) δ 8.05 (s, 1H), 4.40 (q, 2H), 3.24 (t, 2H), 3.17 (t, 2H), 2.96 (s, 3H), 2.10 (t, 2H), 1.39 (t, 3H); MS 293 (M$^+$+1).

What is claimed is:

1. A method of treating a vertebrate which presents with low bone mass comprising administering to said vertebrate a therapeutically effective amount of a compound of Formula II

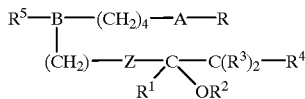

a prodrug thereof or a pharmaceutically acceptable salt of said compound or said prodrug, wherein:

A is ethylene, n-propylene, α-methylethylene, β-methylethylene, α,α-dimethylethylene, β,β-dimethylethylene or oxymethylene;

B is N or C(Q);

R is carboxy, (C$_1$–C$_{10}$) alkoxycarbonyl, carbamoyl, mono-N- or di-N,N-(C$_1$–C$_4$)alkyl-substituted carbamoyl or —COOY wherein Y is 1-succinimidoethyl, 1-pivaloyloxyethyl, 2-acetamidoethyl, diloweralkylaminoloweralkyl, or carbazoyl;

R$^1$ is H, methyl, ethyl or propyl;

R$^2$ is H or (C$_2$–C$_5$) alkanoyl;

R$^3$ is independently H or methyl;

R$^4$ is H, (C$_1$–C$_4$) alkyl, vinyl or 2,2,2-trifluoroethyl; or R$^4$ and R$^1$ are taken together to form a 5–9 membered carbocyclic ring;

R$^5$, when B is C(Q), is formyl, acetyl, pivaloyl, propionyl, acryloyl, hydroxyacetyl, 3-hydroxypropionyl, hydroxymethyl, 1-hydroxyethyl, 1,2-dihydroxyethyl, 1,3-dihydroxypropyl or 1-hydroxyl-1-methylethyl;

R$^5$, when B is N, is formyl, acetyl, propionyl, acryloyl, hydroxyacetyl, 2,2,2-trifluoroethyl or R$^6$SOy;

Z is methylene, ethylene, n-propylene, tetramethylene, vinylene or ethynylene;

Q is H, chloro, bromo, methyl, phenyl or substituted phenyl;

R$^6$ is methyl, ethyl, propyl or isopropyl; and y is 1 or 2.

2. A method of claim 1 wherein osteoporosis, osteotomy, childhood idiopathic bone loss or bone loss associated with periodontitis is treated.

3. A method of claim 2 wherein osteoporosis is treated in a human.

4. A method of claim 3 wherein glucocorticoid-induced osteoporosis, hyperthyroidism-induced osteoporosis, immobilization-induced osteoporosis, heparin-induced osteoporosis or immunosuppressive-induced osteoporosis is treated.

5. A method of claim 1 for augmenting or maintaining bone mass in a vertebrate comprising administering to said vertebrate a therapeutically effective amount of a compound of formula II, a prodrug thereof or a pharmaceutically acceptable salt of said compound or said prodrug.

6. A method of claim 5 wherein bone healing following facial reconstruction, maxillary reconstruction or mandibular reconstruction is treated, vertebral synostosis is induced or long bone extension is enhanced, the healing rate of a bone graft is enhanced or prosthetic ingrowth is enhanced.

7. A method of claim 5 wherein a bone fracture is treated in a human.

8. A method for treating a vertebrate having a condition which presents with low bone mass comprising administering to said vertebrate a. an amount of a compound of formula II

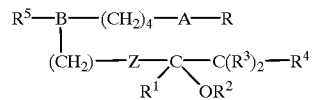

a prodrug thereof or a pharmaceutically acceptable salt of said compound or said prodrug, wherein:

A is ethylene, n-propylene, α-methylethylene, β-methylethylene, α,α-dimethylethylene, β,β-dimethylethylene or oxymethylene;

B is N or C(Q);

R is carboxy, (C$_1$–C$_{10}$) alkoxycarbonyl, carbamoyl, mono-N- or di-N,N-(C$_1$–C$_4$)alkyl-substituted carbamoyl or —COOY wherein Y is 1-succinimidoethyl, 1-pivaloyloxyethyl, 2-acetamidoethyl, diloweralkylaminoloweralkyl, or carbazoyl;

R$^1$ is H, methyl, ethyl or propyl;

R$^2$ is H or (C$_2$–C$_5$) alkanoyl;

R$^3$ is independently H or methyl;

R$^4$ is H, (C$_1$–C$_4$) alkyl, vinyl or 2,2,2-trifluoroethyl; or R$^4$ and R$^1$ are taken together to form a 5–9 membered carbocyclic ring;

R$^5$, when B is C(Q), is formyl, acetyl, pivaloyl, propionyl, acryloyl, hydroxyacetyl, 3-hydroxypropionyl, hydroxymethyl, 1-hydroxyethyl, 1,2-dihydroxyethyl, 1,3-dihydroxypropyl or 1-hydroxyl-1-methylethyl;

R$^5$, when B is N, is formyl, acetyl, propionyl, acryloyl, hydroxyacetyl, 2,2,2-trifluoroethyl or R$^6$SOy;

Z is methylene, ethylene, n-propylene, tetramethylene, vinylene or ethynylene;

Q is H, chloro, bromo, methyl, phenyl or substituted phenyl;

R$^6$ is methyl, ethyl, propyl or isopropyl; and y is 1 or 2; and b. an amount of an anti-resorptive agent, a prodrug thereof or a pharmaceutically acceptable salt of said agent or said prodrug.

9. A method of claim 8 wherein the anti-resorptive agent is droloxifene; raloxifene; tamoxifen; 4-hydroxy-tamoxifen; toremifene; centchroman; levormeloxifene; idoxifene; 6-(4-hydroxy-phenyl)-5-[4-(2-piperidin-1-yl-ethoxy)-benzyl]-naphthalen-2-ol; {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone;

3-(4-(1,2-diphenyl-but-1-enyl)-phenyl)-acrylic acid;

2-(4-methoxy-phenyl)-3-[4-(2-piperidin-1-yl-ethoxy)-phenoxy]benzo[b]thiophen-6-ol;

cis-6-(4-fluoro-phenyl)-5-[4-(2-piperidin-1-yl-ethoxy)-phenyl]-5,6,7,8tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydroisoquinoline, a prodrug thereof or a pharmaceutically acceptable salt of said agent or said prodrug.

10. A method of claim 9 wherein the anti-resorptive agent is tiludronic acid, zoledronic acid, alendronic acid, ibandronic acid, risedronic acid, etidronic acid, clodronic acid, and pamidronic acid, a prodrug thereof or a pharmaceutically acceptable salt of said agent or said prodrug.

11. A method for treating a vertebrate which presents with low bone mass comprising administering to said vertebrate
a. an amount of a compound of formula II

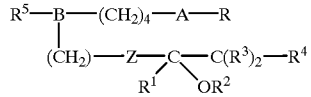

a prodrug thereof or a pharmaceutically acceptable salt of said compound or said prodrug, wherein:

A is ethylene, n-propylene, α-methylethylene, β-methylethylene, α,α-dimethylethylene, β,β-dimethylethylene or oxymethylene;

B is N or C(Q);

R is carboxy, $(C_1-C_{10})$ alkoxycarbonyl, carbamoyl, mono-N- or di-N,N-$(C_1-C_4)$alkyl-substituted carbamoyl or —COOY wherein Y is 1-succinimidoethyl, 1-pivaloyloxyethyl, 2-acetamidoethyl, diloweralkylaminoloweralkyl, or carbazoyl;

$R^1$ is H, methyl, ethyl or propyl;

$R^2$ is H or $(C_2-C_5)$ alkanoyl;

$R^3$ is independently H or methyl;

$R^4$ is H, $(C_1-C_4)$ alkyl, vinyl or 2,2,2-trifluoroethyl; or $R^4$ and $R^1$ are taken together to form a 5–9 membered carbocyclic ring;

$R^5$, when B is C(Q), is formyl, acetyl, pivaloyl, propionyl, acryloyl, hydroxyacetyl, 3-hydroxypropionyl, hydroxymethyl, 1-hydroxyethyl, 1,2-dihydroxyethyl, 1,3-dihydroxypropyl or 1-hydroxyl-1-methylethyl;

$R^5$, when B is N, is formyl, acetyl, propionyl, acryloyl, hydroxyacetyl, 2,2,2-trifluoroethyl or $R^6SOy$;

Z is methylene, ethylene, n-propylene, tetramethylene, vinylene or ethynylene;

Q is H, chloro, bromo, methyl, phenyl or substituted phenyl;

$R^6$ is methyl, ethyl, propyl or isopropyl; and y is 1 or 2; and b. an amount of a bone anabolic agent, a prodrug thereof or a pharmaceutically acceptable salt of said agent or said prodrug.

12. A method of claim 11 wherein said anabolic agent in component b is IGF-1, a bone morphogenetic protein (BMP), a prostaglandin, a prostaglandin agonist/antagonist, sodium fluoride, parathyroid hormone (PTH), an active fragment of parathyroid hormone, a growth hormone or a growth hormone secretagogue, a prodrug thereof or a pharmaceutically acceptable salt of said compound or said prodrug.

13. A method of claim 8 for augmenting and maintaining bone mass in a vertebrate comprising administering to said vertebrate a. an amount of said compound of formula II, a prodrug thereof or a pharmaceutically acceptable salt of said compound or said prodrug; and b. an amount of an anti-resorptive agent, a prodrug thereof or a pharmaceutically acceptable salt of said agent or said prodrug.

14. A method of claim 13 wherein the anti-resorptive agent is droloxifene; raloxifene; tamoxifen; 4-hydroxy-tamoxifen; toremifene; centchroman; levormeloxifene; idoxifene; 6-(4-hydroxy-phenyl)-5-[4-(2-piperidin-1-yl-ethoxy)-benzyl]-naphthalen-2-ol; {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone;

3-(4-(1,2-diphenyl-but-1-enyl)-phenyl)-acrylic acid;

2-(4-methoxy-phenyl)-3-[4-(2-piperidin-1-yl-ethoxy)-phenoxy]-benzo[b]thiophen-6-ol;

cis-6-(4-fluoro-phenyl)-5-[4-(2-piperidin-1-yl-ethoxy)-phenyl]-5,6,7,8-tetrahydronaphthalene-2-ol;

(−)-cis-6-phenyl-5-[4-(2-pyrrolidin-1-yl-ethoxy)-phenyl]-5,6,7,8-tetrahydronaphthalene-2-ol;

cis-6-phenyl-5-[4-(2-pyrrolidin-1-yl-ethoxy)-phenyl]-5,6,7,8-tetrahydronaphthalene-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydroisoquinoline, a prodrug thereof or a pharmaceutically acceptable salt of said agent or said prodrug.

15. A method of claim 14 wherein the anti-resorptive agent is tiludronic acid, zoledronic acid, alendronic acid, ibandronic acid, risedronic acid, etidronic acid, clodronic acid, and pamidronic acid, a prodrug thereof or a pharmaceutically acceptable salt of said agent or said prodrug.

16. A method of claim 11 for augmenting and maintaining bone mass in a vertebrate comprising administering to said vertebrate a. an amount of a compound of formula II, a prodrug thereof or a pharmaceutically acceptable salt of said compound or said prodrug; and b. an amount of a bone anabolic agent, a prodrug thereof or a pharmaceutically acceptable salt of said agent or said prodrug.

17. A method of claim 16 wherein said anabolic agent in component b is IGF-1, a bone morphogenetic protein (BMP), a prostaglandin, a prostaglandin agonist/antagonist, sodium fluoride, parathyroid hormone (PTH), an active fragment of parathyroid hormone, a growth hormone or a growth hormone secretagogue, a prodrug thereof or a pharmaceutically acceptable salt of said compound or said prodrug.

* * * * *